United States Patent
Luk et al.

(10) Patent No.: US 7,217,717 B2
(45) Date of Patent: May 15, 2007

(54) PHENALENE DERIVATIVES

(75) Inventors: Kin-Chun Luk, N. Caldwell, NJ (US); Zhuming Zhang, N. Caldwell, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 541 days.

(21) Appl. No.: 10/852,735

(22) Filed: May 24, 2004

(65) Prior Publication Data

US 2004/0254205 A1      Dec. 16, 2004

Related U.S. Application Data

(60) Provisional application No. 60/477,318, filed on Jun. 10, 2003.

(51) Int. Cl.
*A61K 31/505*    (2006.01)
*A61K 31/519*    (2006.01)
*C07D 471/12*    (2006.01)
*C07D 487/12*    (2006.01)

(52) U.S. Cl. .................. 514/267; 544/242; 544/245; 544/249; 544/250; 514/247; 514/256; 514/257

(58) Field of Classification Search ............... 544/224, 544/242, 245, 249, 250, 251; 514/247, 256, 514/257
See application file for complete search history.

(56) References Cited

U.S. PATENT DOCUMENTS

| 5,610,192 | A * | 3/1997 | Cohen et al. ............... 514/614 |
| 5,747,498 | A | 5/1998 | Schnur et al. |
| 6,548,521 | B1 * | 4/2003 | Cohen et al. ............... 514/354 |
| 2002/0151557 | A1 | 10/2002 | Haddach et al. |

FOREIGN PATENT DOCUMENTS

| EP | 0 566 226 | 10/1993 |
| WO | WO 96/30347 | 10/1996 |
| WO | WO 99/09016 | 2/1999 |
| WO | WO 99/55683 | 11/1999 |
| WO | WO 01/34574 | 5/2001 |

OTHER PUBLICATIONS

Adjei A. A., Drugs of the Future, 2001, vol. 26(11): pp. 1087-1092.
Laird A. D. & Cherrington J. M., Expert Opin. Invetig. Drugs, 2003, vol. 12(1), pp. 51-64.
Laird A. D. & Cherrington J. M., supra; Adjey, supra; Drugs of the Future, 2002, vol. 27(4) pp. 339-345.
Myers, M. R. et al., Bioorganic & Medicinal Chemistry Letters, 1997, vol. 7(4), pp. 421-424.
Bridges A. J. et al., J. Med. Chem. 1996, vol. 39 pp. 267-276.
Rewcastle G. W. et al., J. Med. Chem., 1995, vol. 38, pp. 3482-3487.
Rusnak, D. W. et al., Cancer Research, American Association for Cancer Research Baltimore MD, US vol. 61 No. 19, Oct. 1, 2001, p. 7196-7203.
Traxler et al., Expert Opinion on Therapeutic Patents, Ashley Publications, GB, vol. 7, No. 6, 1997 p. 571-588.

* cited by examiner

*Primary Examiner*—Golam M. M. Shameem
(74) *Attorney, Agent, or Firm*—George W. Johnston; Patricia S. Rocha-Tramaloni

(57) ABSTRACT

Novel 1,3,4-triaza-phenalene and 1,3,4,6-tetraazaphenalene derivatives are disclosed. These compounds inhibit epidermal growth factor receptor ("EGFR") tyrosine kinase. These compounds and their pharmaceutically acceptable salts and esters have antiproliferative activity and are useful, inter alia, in the treatment or control of cancer, in particular solid tumors. This invention also relates to pharmaceutical compositions containing such compounds and to methods of treating or controlling cancer, most particularly the treatment or control of breast, lung, colon and prostate tumors.

22 Claims, No Drawings

PHENALENE DERIVATIVES

PRIORITY TO RELATED APPLICATIONS

This application claims the benefit of Provisional Application Ser. No. 60/477,318, filed Jun. 10, 2003.

FIELD OF THE INVENTION

The present invention relates to novel 1,3,4-triaza-phenalene and 1,3,4,6-tetraazaphenalene derivatives that inhibit epidermal growth factor receptor ("EGFR") tyrosine kinase. These compounds and their pharmaceutically acceptable salts and esters have antiproliferative activity and are useful, inter alia, in the treatment or control of cancer, in particular solid tumors. This invention also relates to pharmaceutical compositions containing such compounds and to methods of treating or controlling cancer, most particularly the treatment or control of breast, lung, colon and prostate tumors. Finally, this invention is also directed to novel intermediate compounds useful in the preparation of the novel phenalene derivatives herein disclosed.

BACKGROUND OF THE INVENTION

Receptor tyrosine kinases are transmembrane proteins that participate in cell signal transduction. Specifically, they transmit growth factor signals from the cell surface to certain intracellular processes that control critical function such as growth, differentiation and angiogenesis. A. A. Adjei, Drugs of the Future 2001, 26(11):1087–1092.

Many cancers are associated with aberrant signaling. In particular, deregulated signaling via tyrosine kinases plays a key role in the growth and spread of cancers. A. D. Laird and J. M. Cherrington, Expert Opin. Invetig. Drugs, 2003, 12(1): 51–64. One family of receptor tyrosine kinases is the epidermal growth factor receptor (EGFR) tyrosine kinase. These receptors have been found to be over expressed in a number of epithelial cancers and have been implicated in tumor aggressiveness.

The role of receptor tyrosine kinases (RTKs), and in particular of EGFR, in the growth and spread of cancers is well established. See, Laird and Cherrington, supra; and Adjey, supra. There is thus extensive research to develop small molecule inhibitors of RTKs, and in particular of EGFR. For reviews of compounds inhibiting EGFR and their therapeutic use see Laird and Cherrington, supra; Adjey, supra; Drugs of the Future 2002, 27(4):339–345; M. R. Myers et al., Bioorganic & Medicinal Chemistry Letters, 1997, 7(4): 421–424; A. J. Bridges et al., J. Med. Chem., 1996, 39:267–276; G. W. Rewcastle et al., J. Med. Chem. 1995, 38:3482–3487

SUMMARY OF THE INVENTION

The present invention relates to novel 1,3,4-triaza-phenalene and 1,3,4,6-tetraazaphenalene derivatives of the formula

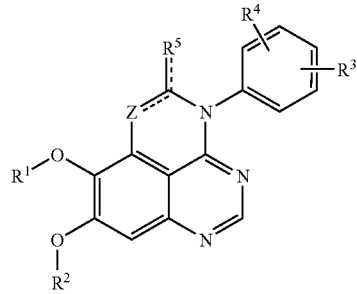

I wherein
Z is C or N;
$R^1$ and $R^2$ are independently selected from
 H,
 lower alkyl,
 lower alkyl substituted with
  $OR^6$,
  $NR^6R^7$,
  heterocycle, and
  heteroaryl;
$R^3$ and $R^4$ are each independently selected from
 H,
 F,
 Cl, and
 Br;
$R^5$ is selected from
 H,
 OH,
 SH,
 oxo,
 thione, and
 $C_1$–$C_3$ alkyl; and
$R^6$ and $R^7$ are each independently selected from
 H, and
 lower alkyl
 or, alternately $NR^6R^7$ together can form a ring having 3 to 7 atoms, said ring optionally including up to three additional heteroatoms and being optionally substituted by one or more lower alkyl;
or the pharmaceutically acceptable salts or esters thereof.

The dotted lines in the above formula signify that a double bond exists either between Z and the carbon atom to which $R^5$ is attached or between the carbon atom and $R^5$. Use of dotted lines to depict tautomeric forms is well known in the art.

These compounds inhibit epidermal growth factor receptor ("EGFR") tyrosine kinase. These compounds and their pharmaceutically acceptable salts and esters have antiproliferative activity and are useful, inter alia, in the treatment or control of cancer, in particular solid tumors.

The present invention also relates to pharmaceutical compositions comprising one or more compounds of the invention, or a pharmaceutically acceptable salt or ester thereof, and a pharmaceutically acceptable carrier or excipient.

The present invention further relates to a method for treating or controlling cancer, more particularly the treatment or control of a solid tumor, most particularly to the treatment or control of breast, lung and colon and prostate tumors by administering to a patient in need of such therapy a therapeutically effective amount of a compound of formula I, or a pharmaceutically acceptable salt or ester thereof.

Finally, this invention also relates to novel intermediate compounds useful in the preparation of a compound of formula I.

DETAILED DESCRIPTION OF THE INVENTION

Definitions

As used herein, the following terms shall have the following definitions.

"Alkyl" alone or in conjunction with another term, e.g. alkyl-heterocycle, denotes a straight-chain or branched saturated aliphatic hydrocarbon having 1 to 12, preferably 1 to 10, carbon atoms. Preferred alkyl groups are "lower alkyl" groups having 1 to 6, preferably 1 to 4, carbon atoms. Typical lower alkyl groups include methyl, ethyl, propyl, isopropyl, butyl, t-butyl, 2-butyl, pentyl, hexyl and the like. As used herein, $C_1$–$C_3$ alkyl means an alkyl group having 1 to 3 carbon atoms.

"Aryl" alone or in conjunction with another term means a monovalent, monocyclic or bicyclic, aromatic carbocyclic hydrocarbon radical, preferably a 6–10 membered aromatic aromatic ring system. Preferred aryl groups include, but are not limited to, phenyl, naphthyl, tolyl and xylyl.

"Effective amount" means an amount that is effective to prevent, alleviate or ameliorate symptoms of disease or prolong the survival of the subject being treated.

"Halogen" means fluorine, chlorine, bromine or iodine, preferably fluorine, chlorine or bromine.

"Hetero atom" means an atom selected from N, O and S.

"Heteroaryl" means an aromatic heterocyclic ring system containing up to two rings. Preferred heteroaryl groups include, but are not limited to, thienyl, furyl, indolyl, pyrrolyl, pyridinyl, pyridine, pyrazinyl, oxazolyl, thiaxolyl, quinolinyl, pyrimidinyl, imidazole and tetrazolyl.

"Heterocycle" or "heterocyclyl" means a saturated or partially unsaturated, non-aromatic cyclic radical of 3 to 8 ring atoms in which from one to 4 ring atoms are hetero atoms selected from nitrogen, oxygen, sulfur, or a combination thereof, the remaining ring atoms being C. Examples of preferred heterocycles are piperidine, piperazine, pyrrolidine, morpholine, indoline, tetrahydropyranyl, thiomorpholino, pentamethylene sulfide, and pentamethylene sulfone.

"$IC_{50}$" refers to the concentration of a particular compound according to the invention required to inhibit 50% of a specific measured activity. $IC_{50}$ can be measured, inter alia, as is described in Example 23, infra.

"Oxo" means =O.

"Pharmaceutically acceptable ester" refers to a conventionally esterified compound of formula I having an alcohol or a carboxyl group, which esters retain the biological effectiveness and properties of the compounds of formula I and are cleaved in vivo (in the organism) to the corresponding active alcohol or carboxylic acid. Examples of ester groups which are cleaved (in this case hydrolyzed) in vivo to the corresponding carboxylic acids ($R^{40}C(=O)OH$) are lower alkyl esters which may be substituted with $NR^{41}R^{42}$ where $R^{41}$ and $R^{42}$ are lower alkyl, or where $NR^{41}R^{42}$ taken together form a monocyclic aliphatic heterocycle, such as pyrrolidine, piperidine, morpholine, N-methylpiperazine, etc.; and carbonate esters of the formula $R^{40}C(=O)OCHR^{43}OC(=O)$, where $R^{43}$ is hydrogen or methyl.

Examples of lower alkyl esters are the acetyl, propionyl esters, and the like. Examples of lower alkyl esters substituted with $NR^{41}R^{42}$ are the diethylaminoacetyl, 2-(4-morpholinyl)acetyl, 2-(4-methylpiperazin-1-yl)acetyl esters, and the like. Examples of carbonate esters are acetoxymethoxy-formyl and 2-(dimethylamino)acetoxy-methoxyformyl esters.

Further information concerning examples of and the use of esters for the delivery of pharmaceutical compounds is available in Design of Prodrugs. Bundgaard H ed. (Elsevier, 1985). See also, H. Ansel et. al., Pharmaceutical Dosage Forms and Drug Delivery Systems (6th Ed. 1995) at pp. 108–109; Krogsgaard-Larsen, et. al., Textbook of Drug Design and Development (2d Ed. 1996) at pp. 152–191; H. Gao et al., Synthesis 2000, 329–351; J. Alexander et al., J. Med. Chem. 1988, 31, 318–322.

"Pharmaceutically acceptable salt" refers to conventional acid-addition salts or base-addition salts that retain the biological effectiveness and properties of the compounds of formula I and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluene sulfonic acid, salicylic acid, methanesulfonic acid, oxalic acid, succinic acid, citric acid, malic acid, lactic acid, fumaric acid, and the like. Sample base-addition salts include those derived from ammonium, potassium, sodium and, quaternary ammonium hydroxides, such as for example, tetramethylammonium hydroxide. The chemical modification of a pharmaceutical compound (i.e. drug) into a salt is a technique well known to pharmaceutical chemists to obtain improved physical and chemical stability, hygroscopicity, flowability and solubility of compounds. See, e.g., H. Ansel et. al., Pharmaceutical Dosage Forms and Drug Delivery Systems (6th Ed. 1995) at pp. 196 and 1456–1457.

"Pharmaceutically acceptable," such as pharmaceutically acceptable carrier, excipient, etc., means pharmacologically acceptable and substantially non-toxic to the subject to which the particular compound is administered.

"Substituted," as in alkyl substituted with, means that the substitution can occur at one or more positions and, unless otherwise indicated, that the substituents at each substitution site are independently selected from the specified options.

"Therapeutically effective amount" means an amount of at least one compound of Formula I, or a pharmaceutically acceptable salt or ester thereof, that significantly inhibits proliferation and/or prevents differentiation of a human tumor cell, including human tumor cell lines.

"Thione" signifies a =S at a non-terminal carbon atom.

In one embodiment, the present invention relates to compounds of formula

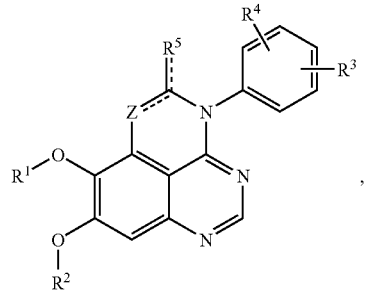

I or the pharmaceutically acceptable salts or esters thereof, wherein Z and $R^1$ to $R^5$ are as defined above.

In a preferred embodiment of the compounds of formula I, Z is N. In another preferred embodiment, Z is C.

In another preferred embodiment of the compounds of formula I, $R^1$ and $R^2$ are independently lower alkyl, preferably methyl. In a most preferred embodiment, both $R^1$ and $R^2$ are methyl.

In another preferred embodiment of the compounds of formula I, $R^3$ and $R^4$ are independently selected from H, Br, Cl, and F, most preferably H. In a most preferred embodiment, $R^3$ and $R^4$ are both H.

In another preferred embodiment of the compounds of formula I, $R^5$ is selected from =O, =S, H and lower alkyl, most preferably H and lower alkyl.

The following compounds are preferred embodiments according to the instant invention:

8,9-Dimethoxy-3-phenyl-1H,3H-1,3,4,6-tetraaza-phenalen-2-one (Example 1D);
8,9-Dimethoxy-3-phenyl-1H,3H-1,3,4,6-tetraaza-phenalene-2-thione (Example 2);
8,9-Dimethoxy-3-phenyl-3H-1,3,4,6-tetraaza-phenalene (Example 3);
8,9-Dimethoxy-2-methyl-3-phenyl-3H-1,3,4,6-tetraaza-phenalene (Example 4);
2-Ethyl-8,9-dimethoxy-3-phenyl-3H-1,3,4,6-tetraaza-phenalene (Example 5);
3-(3-Bromo-phenyl)-8,9-dimethoxy-3H-1,3,4,6-tetraaza-phenalene (Example 6C);
3-(3-Bromo-phenyl)-8,9-dimethoxy-1H,3H-1,3,4,6-tetraaza-phenalen-2-one (Example 7);
3-(3-Bromo-phenyl)-8,9-dimethoxy-2-methyl-3H-1,3,4,6-tetraaza-phenalene (Example 8);
3-(3-Bromo-phenyl)-8,9-dimethoxy-1H,3H-1,3,4,6-tetraaza-phenalen-2-thione (Example 9);
3-(3-Bromo-phenyl)-2-ethyl-8,9-dimethoxy-3H-1,3,4,6-tetraaza-phenalene (Example 10);
3-(3-Chloro-phenyl)-8,9-dimethoxy-1H,3H-1,3,4,6-tetraaza-phenalen-2-one (Example 11C);
3-(3-Chloro-phenyl)-8,9-dimethoxy-2-methyl-3H-1,3,4,6-tetraaza-phenalene (Example 12);
3-(4-Chloro-phenyl)-8,9-dimethoxy-3H-1,3,4,6-tetraaza-phenalene (Example 13C);
3-(4-Chloro-phenyl)-8,9-dimethoxy-1H,3H-1,3,4,6-tetraaza-phenalen-2-thione (Example 14);
7,8-Dimethoxy-5-methyl-4-phenyl-4H-1,3,4-triaza-phenalene (Example 15G);
4-(4-Chloro-phenyl)-7,8-dimethoxy-5-methyl-4H-1,3,4-triaza-phenalene (Example 16G);
4-(3-Bromo-phenyl)-7,8-dimethoxy-5-methyl-4H-1,3,4-triaza-phenalene (Example 17G);
4-(3-Bromo-phenyl)-7,8-dimethoxy-5-methyl-4H-1,3,4-triaza-phenalene (Example 18G);
4-(4-Bromo-2-fluoro-phenyl)-7,8-dimethoxy-5-methyl-4H-1,3,4-triaza-phenalene (Example 19G);
7,8-Dimethoxy-4-phenyl-4H-1,3,4-triaza-phenalene (Example 20B);
4-(4-Chloro-phenyl)-7,8-dimethoxy-4H-1,3,4-triaza-phenalene (Example 21B); and
4-(3-Bromo-phenyl)-7,8-dimethoxy-4H-1,3,4-triaza-phenalene (Example 22B).

The compounds disclosed herein and covered by formula I above may exhibit tautomerism or structural isomerism. It is intended that the invention encompasses any tautomeric or structural isomeric form of these compounds, or mixtures of such forms, and is not limited to any one tautomeric or structural isomeric form depicted in the formula above.

General Synthesis of Compounds According to the Invention

The compounds of the present invention can be prepared by any conventional means. Suitable processes for synthesizing these compounds are provided in the examples. Generally, compounds of formula I can be prepared according to one of the below-described synthetic routes.

Scheme 1

Scheme 2

Scheme 3
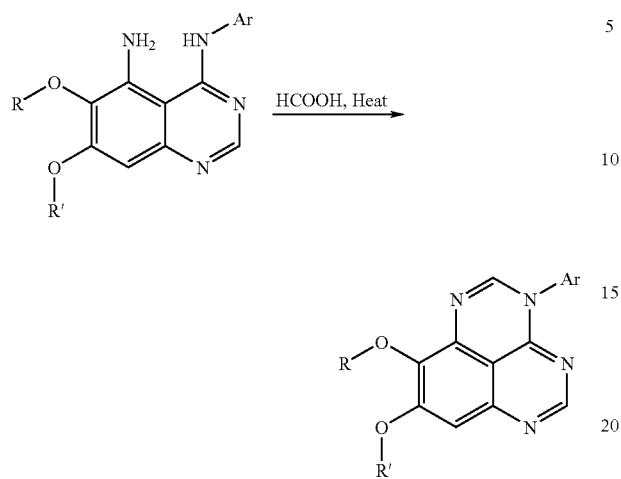
Scheme 4
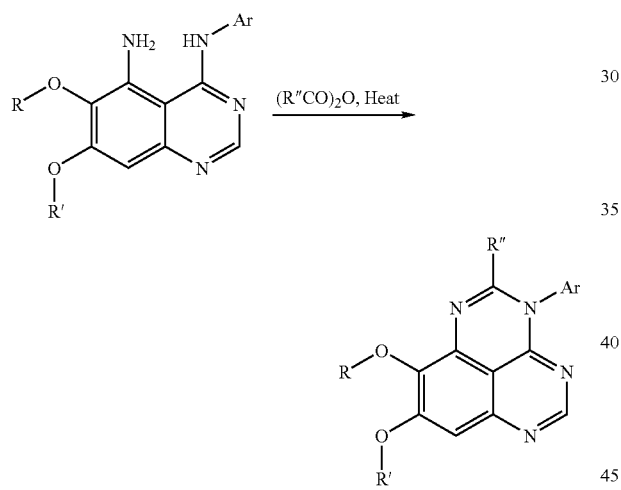
Scheme 5
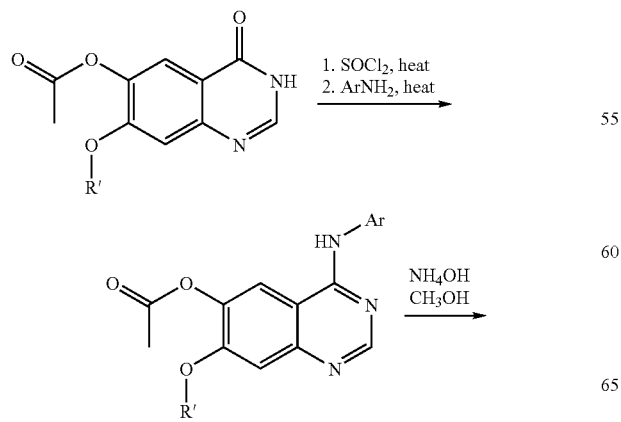
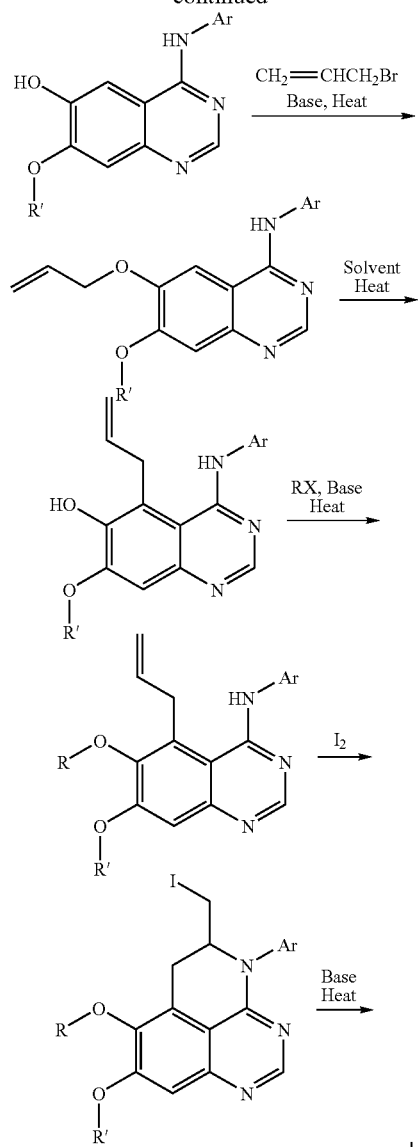
Scheme 6
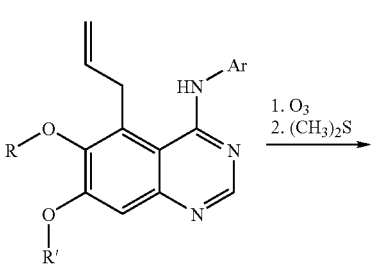

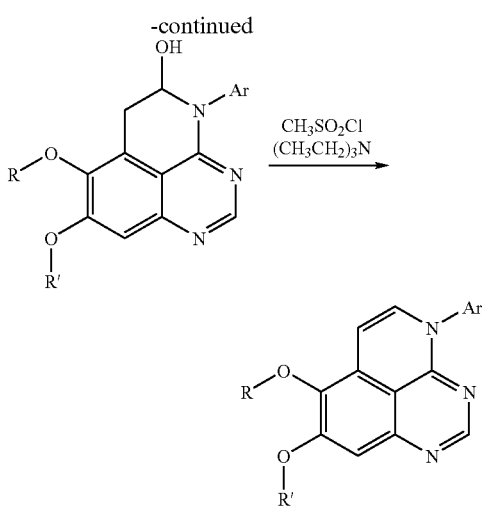

Separating a Mixture of Stereoisomers into the Optically Pure Stereoisomers (when Compound of Formula I is Chiral)

The optional separation of isomeric structures of formula I can be carried out according to known methods such as for example resolution or chiral high-pressure liquid chromatography (also known as chiral HPLC). Resolution methods are well known, and are summarized in "Enantiomers, Racemates, and Resolutions" (Jacques, J. et al. John Wiley and Sons, NY, 1981). Methods for chiral HPLC are also well known, and are summarized in "Separation of Enantiomers by Liquid Chromatographic Methods" (Pirkle, W. H. and Finn, J. in "Asymmetric Synthesis", Vol. 1, Morrison, J. D., Ed., Academic Press, Inc., NY 1983, pp. 87–124).

Converting a Compound of Formula I that Bears a Basic Nitrogen into a Pharmaceutically Acceptable Acid Addition Salt The optional conversion of a compound of formula I that bears a basic nitrogen into a pharmaceutically acceptable acid addition salt can be effected by conventional means. For example, the compound can be treated with an inorganic acid such as for example hydrochloric acid, hydrobromic acid, sulfuric acid, nitric acid, phosphoric acid, or with an appropriate organic acid such as acetic acid, citric acid, tartaric acid, methanesulfonic acid, p-toluene sulfonic acid, or the like.

Converting a Compound of Formula I that Bears a Carboxylic Acid Group into a Pharmaceutically Acceptable Alkali Metal Salt The optional conversion of a compound of formula I that bears a carboxylic acid group into a pharmaceutically acceptable alkali metal salt can be effected by conventional means. For example, the compound can be treated with an inorganic base such as lithium hydroxide, sodium hydroxide, potassium hydroxide, or the like.

Converting a Compound of Formula I that Bears an Alcohol or a Carboxylic Acid Group into a Pharmaceutically Acceptable Ester The optional conversion of a compound of formula I that bears an alcohol or a carboxylic acid group into a pharmaceutically acceptable ester can be effected by conventional means. The conditions for the formation of the ester will depend on the stability of the other functional groups in the molecule to the reaction conditions. If the other moieties in the molecule are stable to acidic conditions, the ester may be conveniently prepared by heating in a solution of a mineral acid (e.g., sulfuric acid) in an alcohol. Alternatively, the ester may be prepared by the condensation of an alcohol with an acid anhydride or an acid halide under conditions known in the art. Other methods of preparing the ester, which may be convenient if the molecule is not stable to acidic conditions include treating the compound with an alcohol and acid in the presence of a coupling agent and in the optional presence of additional agents that may accelerate the reaction. Many such coupling agents are known to one skilled in the art of organic chemistry. Two examples are dicyclohexylcarbodiimide and triphenylphosphine/diethyl azodicarboxylate. In the case where dicyclohexylcarbodiimide is used as the coupling agent, the reaction is conveniently carried out by treating the acid with the alcohol, dicyclohexylcarbodiimide, and the optional presence of a catalytic amount (0–10 mole %) of N,N-dimethylaminopyridine, in an inert solvent such as a halogenated hydrocarbon (e.g., dichloromethane) at a temperature between about 0 degree and about room temperature, preferably at about room temperature. In the case where triphenylphosphine/diethyl azodicarboxylate is used as the coupling agent, the reaction is conveniently carried out by treating the acid with the alcohol, triphenylphosphine and diethyl azodicarboxylate, in an inert solvent such as an ether (e.g., tetrahydrofuran) or an aromatic hydrocarbon (e.g., benzene) at a temperature between about 0 degrees and about room temperature, preferably at about 0 degree.

Compositions/Formulations

In an alternative embodiment, the present invention includes pharmaceutical compositions comprising at least one compound of formula I, or a pharmaceutically acceptable salt or ester thereof and a pharmaceutically acceptable excipient and/or carrier.

These pharmaceutical compositions can be administered orally, for example in the form of tablets, coated tablets, dragees, hard or soft gelatin capsules, solutions, emulsions or suspensions. They can also be administered rectally, for example, in the form of suppositories, or parenterally, for example, in the form of injection solutions.

The pharmaceutical compositions of the present invention comprising compounds of formula I, and/or the salts or esters thereof, may be manufactured in a manner that is known in the art, e.g. by means of conventional mixing, encapsulating, dissolving, granulating, emulsifying, entrapping, dragee-making, or lyophilizing processes. These pharmaceutical preparations can be formulated with therapeutically inert, inorganic or organic carriers. Lactose, corn starch or derivatives thereof, talc, steric acid or its salts can be used as such carriers for tablets, coated tablets, dragees and hard gelatin capsules. Suitable carriers for soft gelatin capsules include vegetable oils, waxes and fats. Depending on the nature of the active substance, no carriers are generally required in the case of soft gelatin capsules. Suitable carriers for the manufacture of solutions and syrups are water, polyols, saccharose, invert sugar and glucose. Suitable carriers for injection are water, alcohols, polyols, glycerine, vegetable oils, phospholipids and surfactants. Suitable carriers for suppositories are natural or hardened oils, waxes, fats and semi-liquid polyols.

The pharmaceutical preparations can also contain preserving agents, solubilizing agents, stabilizing agents, wetting agents, emulsifying agents, sweetening agents, coloring agents, flavoring agents, salts for varying the osmotic pressure, buffers, coating agents or antioxidants. They can also contain other therapeutically valuable substances, including additional active ingredients other than those of formula I.

Dosages

As mentioned above, the compounds of the present invention, including the compounds of formula I, are useful in the treatment or control of cell proliferative disorders, including chemoprevention of cancer. Chemoprevention is defined as inhibiting the development of invasive cancer by either blocking the initiating mutagenic event or by blocking the progression of pre-malignant cells that have already suffered an insult or inhibiting tumor relapse. These compounds and formulations containing said compounds are particularly useful in the treatment or control of solid tumors, such as, for example, breast, colon, lung and prostate tumors.

A therapeutically effective amount of a compound in accordance with this invention means an amount of compound that is effective to prevent, alleviate or ameliorate symptoms of disease or prolong the survival of the subject being treated. Determination of a therapeutically effective amount is within the skill in the art.

The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 10 mg to about 10,000 mg, preferably from about 200 mg to about 1,000 mg, should be appropriate, although the upper limit may be exceeded when indicated. The daily dosage can be administered as a single dose or in divided doses, or for parenteral administration, it may be given as continuous infusion.

Combinations

The compounds of this invention may be used in combination (administered in combination or sequentially) with known anti-cancer treatments such as radiation therapy or with cytostatic or cytotoxic agents, such as for example, but not limited to, DNA interactive agents, such as cisplatin or doxorubicin; topoisomerase II inhibitors such as etoposide: topoisomerase I inhibitors such as CPT-11 or topotecan; tubulin interacting agents, such as paclitaxel, docetaxel or epothilones; hormonal agents such as tamoxifen; thymidilate synthase inhibitors, such as 5-fluorouracil; and anti-metabolites such as methotrexate. Compounds of formula I may also be useful in combination with modulators of p53 transactivation.

If formulated as a fixed dose, the above-described combination products include the compounds of this invention within the dosage range described above and the other pharmaceutically active agent or treatment within its approved dose range. Compounds of formula I may also be administered sequentially with known anticancer or cytotoxic agents when concomitant administration or a combination is inappropriate. This invention is not limited in the sequence of administration: compounds of formula I may be administered either prior to or after administration of the known anticancer or cytotoxic agent.

Intermediates

In another embodiment, the present invention also relates to novel intermediates useful in the preparation of compounds of formula I. These novel intermediates include the following compounds:

(5-Allyl-6,7-dimethoxy-quinazolin-4-yl)-phenyl-amine (Example 15E);

5-Iodomethyl-7,8-dimethoxy-4-phenyl-5,6-dihydro-4H-1,3,4-triaza-phenalene (Example 15F);

5-Allyl-4-(4-chloro-phenylamino)-7-methoxy-quinazolin-6-ol (Example 16D);

(5-Allyl-6,7-dimethoxy-quinazolin-4-yl)-(4-chloro-phenyl)-amine (Example 16E);

4-(4-Chloro-phenyl)-5-iodomethyl-7,8-dimethoxy-5,6-dihydro-4H-1,3,4-triaza-phenalene (Example 16F);

5-Allyl-4-(3-bromo-phenylamino)-7-methoxy-quinazolin-6-ol (Example 17D);

(5-Allyl-6,7-dimethoxy-quinazolin-4-yl)-(3-bromo-phenyl)-amine (Example 17E);

4-(3-Bromo-phenyl)-5-iodomethyl-7,8-dimethoxy-5,6-dihydro-4H-1,3,4-triaza-phenalene (Example 17F);

5-Allyl-4-(3-chloro-4-fluoro-phenylamino)-7-methoxy-quinazolin-6-ol (Example 18D);

(5-Allyl-6,7-dimethoxy-quinazolin-4-yl)-(3-chloro-4-fluoro-phenyl)-amine (Example 18E);

4-(3-Chloro-4-fluoro-phenyl)-5-iodomethyl-7,8-dimethoxy-5,6-dihydro-4H-1,3,4-triaza-phenale (Example 18F);

5-Allyl-4-(4-bromo-2-fluoro-phenylamino)-7-methoxy-quinazolin-6-ol (Example 19D);

(5-Allyl-6,7-dimethoxy-quinazolin-4-yl)-(4-bromo-2-fluoro-phenyl)-amine (Example 19E);

4-(4-Bromo-2-fluoro-phenyl)-5-iodomethyl-7,8-dimethoxy-5,6-dihydro-4H-1,3,4-triaza-phenalen (Example 19F);

7,8-Dimethoxy-4-phenyl-5,6-dihydro-4H-1,3,4-triaza-fennel-5-ol (Example 20A);

7,8-Dimethoxy-4-phenyl-5,6-dihydro-4H-1,3,4-triaza-fennel-5-ol (Example 21A); and 7,8-Dimethoxy-4-(3-bromo-phenyl)-5,6-dihydro-4H-1,3,4-triaza-fennel-5-ol (Example 22A).

EXAMPLES

The following examples illustrate preferred methods for synthesizing and using the compounds and formulations of the present invention. These examples and preparations are illustrative and are not intended to be limiting. It should be understood that there may be other embodiments that fall within the spirit and scope of the invention as defined by the claims appended hereto.

Abbreviations Used in the Examples:
DMF N,N-dimethylformamide
TLC thin layer chromatography
DBU 1,8-diazabicyclo[5.4.0]under-7-ene

Example 1

8,9-Dimethoxy-3-phenyl-1H,3H-1,3,4,6-tetraaza-phenalen-2-one

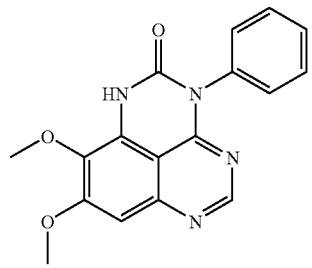

C$_{17}$H$_{14}$N$_4$O$_3$
MW 322.33

Step A: 6,7-Dimethoxy-5-nitro-3H-quinazolin-4-one

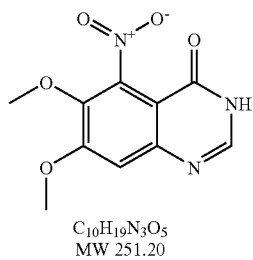

C$_{10}$H$_{19}$N$_3$O$_5$
MW 251.20

6,7-Dimethoxy-5-nitro-3H-quinazolin-4-one was prepared as a pale yellow solid according to the procedure of Cho, Qui; Ding, Lynn; Shi, Hsiencheng; Leoni, Lorenzo M.; Genini, Davide; Carson, Dennis A.; Cottam, Howard B.; *J. Med. Chem.*, 1999, 42, 3860–3873.

Step B: (6,7-Dimethoxy-5-nitro-quinazolin-4-yl)-phenyl-amine

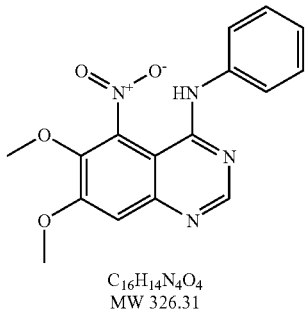

C$_{16}$H$_{14}$N$_4$O$_4$
MW 326.31

To a solution of 6,7-dimethoxy-5-nitro-3H-quinazolin-4-one (1.0 g, 3.98 mmol) (from Example 1, Step A, supra) in SOCl$_2$ (20 mL) (Aldrich) were added a few drops of DMF. The reaction mixture was then heated with stirring at 90° C. for 3 hours. The solvents were evaporated and the residue was dried in vacuo. The residue was dissolved in 2-propanol (30 mL), then aniline (0.36 mL, 3.98 mmol) (Aldrich) was added. The reaction mixture was heated at 110° C. for 3 hours. The reaction mixture was concentrated under reduced pressure and the residue was purified by chromatography using EtOAc/CH$_2$Cl$_2$/NEt$_3$ (1:1:0.05) as eluent to give the desired (6,7-dimethoxy-5-nitro-quinazolin-4-yl)-phenyl-amine as a yellow solid. (Yield 0.9 g, 70%).

Step C: 6,7-Dimethoxy-N4-phenyl-quinazoline-4,5-diamine

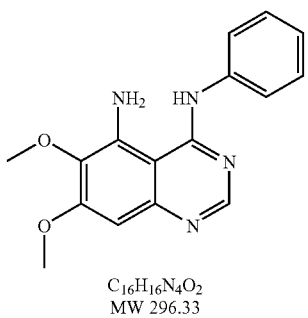

C$_{16}$H$_{16}$N$_4$O$_2$
MW 296.33

To a solution of (6,7-dimethoxy-5-nitro-quinazolin-4-yl)-phenyl-amine (1.0 g, 3.14 mmol) (from Example 1, Step B, supra), NH$_4$Cl (1.7 g, 31.4 mmol) in MeOH, H$_2$O and CHCl$_3$ (40 mL, 2:1:1) was added Zn powder (2.0 g, 31.4 mmol) (Aldrich). The reaction mixture was stirred at room temperature for 1 hour. The mixture was then filtered, the filtrate was concentrated and then extracted with chloroform (100 mL). The organic layer was separated, dried over Na$_2$SO$_4$, and concentrated. The residue was purified by chromatography using EtOAc/CH$_2$Cl$_2$ (1:1) as eluent to give the desired 6,7-dimethoxy-N 4-phenyl-quinazoline-4,5-diamine as a yellow gum. (Yield 0.5 g, 54%).

Step D: 8,9-Dimethoxy-3-phenyl-1H,3H-1,3,4,6-tetraaza-phenalen-2-one

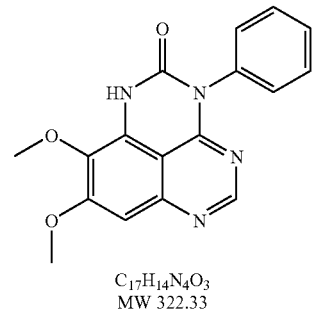

C$_{17}$H$_{14}$N$_4$O$_3$
MW 322.33

To a solution of 6,7-dimethoxy-N4-phenyl-quinazoline-4,5-diamine (0.2 g, 0.68 mmol) (from Example 1, Step C, supra) in 1,2-dichloroethane (50 mL) was added 1,1'-carbonyldiimidazole (0.55 g, 3.4 mmol) (Aldrich). The reaction mixture was heated with stirring at 90° C. for 4 hours. The solvent was evaporated and the residue was purified by chromatography using EtOAc/CH$_2$Cl$_2$/Et$_3$N (1:1:0.04) as eluent to give the desired 8,9-dimethoxy-3-phenyl-1H,3H-1,3,4,6-tetraaza-phenalen-2-one as a yellow solid. (Yield 0.13 g, 59%).

Example 2

8,9-Dimethoxy-3-phenyl-1H,3H-1,3,4,6-tetraaza-phenalene-2-thione

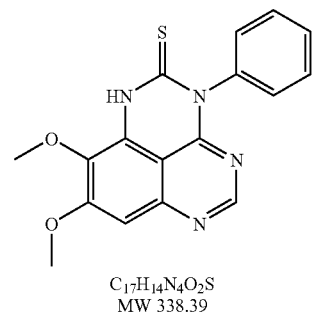

C$_{17}$H$_{14}$N$_4$O$_2$S
MW 338.39

To a solution of 6,7-dimethoxy-N4-phenyl-quinazoline-4,5-diamine (80 mg, 0.27 mmol) (from Example 1, Step, C supra) in 1,2-dichloroethane (30 mL) was added 1,1'-thiocarbonyldiimidazole (0.58 g, 3.24 mmol) (Fluka). The reaction mixture was heated with stirring at 80° C. for 4 hours. The solvent was evaporated and the residue was purified by chromatography using EtOAc/CH$_2$Cl$_2$/Et$_3$N (1:1:0.04) as eluent to give the desired 8,9-dimethoxy-3-phenyl-1H,3H-1,3,4,6-tetraaza-phenalene-2-thione as a gray solid. (Yield 50 mg (55%).

Example 3

8,9-Dimethoxy-3-phenyl-3H-1,3,4,6-tetraaza-phenalene

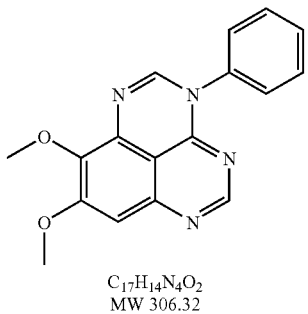

C$_{17}$H$_{14}$N$_4$O$_2$
MW 306.32

A solution of 6,7-dimethoxy-N4-phenyl-quinazoline-4,5-diamine (80 mg, 0.27 mmol) (from Example 1, Step C, supra) in formic acid (5 mL) was heated at 110° C. for 2 hours. Aqueous NaOH solution was then added to the reaction mixture to a pH 10–12. The solution was diluted with chloroform (50 mL). The organic layer was separated, dried over Na$_2$SO$_4$, and concentrated. This residue was purified by chromatography using EtOAc/Et$_3$N (1:0.04) as eluent to give the desired 8,9-dimethoxy-3-phenyl-3H-1,3,4,6-tetraaza-phenalene as a white solid. (Yield 45 mg, 54%).

Example 4

8,9-Dimethoxy-2-methyl-3-phenyl-3H-1,3,4,6-tetraaza-phenalene

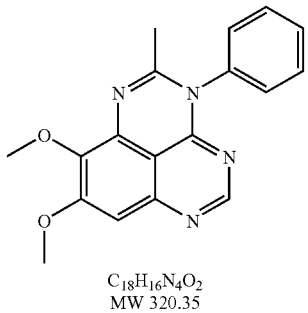

C$_{18}$H$_{16}$N$_4$O$_2$
MW 320.35

A solution of 6,7-dimethoxy-N4-phenyl-quinazoline-4,5-diamine (60 mg, 0.20 mmol) (from Example 1, Step C, supra) in acetic anhydride (2 mL) was heated at 150° C. for 2 hours. Aqueous NaOH solution was then added to the reaction mixture to a pH 10–12. The solution was diluted with chloroform (50 mL). The organic layer was separated, dried over Na$_2$SO$_4$, and concentrated. The residue was purified by chromatography using EtOAc/Et$_3$N (1:0.04) as eluent to give the desired 8,9-dimethoxy-2-methyl-3-phenyl-3H-1,3,4,6-tetraaza-phenalene as a yellow solid. (Yield 20 mg, 62%).

Example 5

2-Ethyl-8,9-dimethoxy-3-phenyl-3H-1,3,4,6-tetraaza-phenalene

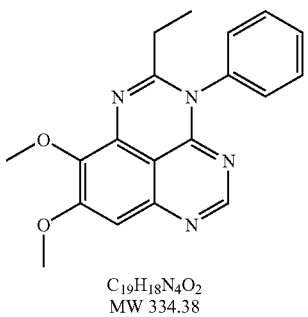

C$_{19}$H$_{18}$N$_4$O$_2$
MW 334.38

A solution of 6,7-dimethoxy-N4-phenyl-quinazoline-4,5-diamine (130 mg, 0.44 mmol) (from Example 1, Step C, supra) in propionic anhydride (3 mL) (Aldrich) was heated at 170° C. for 2 hours. Aqueous NaOH solution was added to the reaction mixture to a pH 10–12. The solution was diluted with chloroform (50 mL). The organic layer was separated, dried over Na$_2$SO$_4$, and concentrated. This residue was purified by chromatography using EtOAc/Et$_3$N (1:0.05) as eluent to give the desired 2-ethyl-8,9-dimethoxy-3-phenyl-3H-1,3,4,6-tetraaza-phenalene as an orange solid. (Yield 21 mg, 14%).

Example 6

3-(3-Bromo-phenyl)-8,9-dimethoxy-3H-1,3,4,6-tetraaza-phenalene

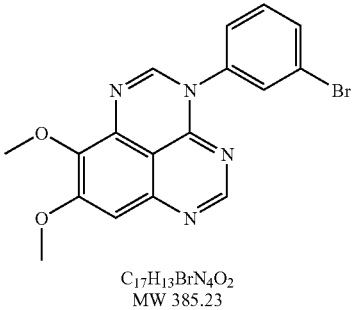

C$_{17}$H$_{13}$BrN$_4$O$_2$
MW 385.23

Step A: (3-Bromo-phenyl)-(6,7-dimethoxy-5-nitro-quinazolin-4-yl)-amine

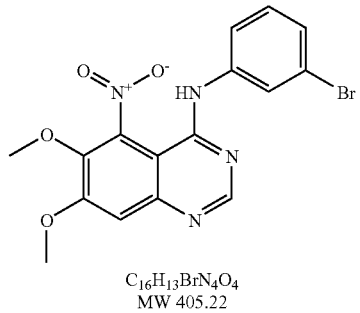

C₁₆H₁₃BrN₄O₄
MW 405.22

To a solution of 6,7-dimethoxy-5-nitro-3H-quinazolin-4-one (1.0 g, 3.98 mmol) (from Example 1, Step A, supra) in SOCl₂ (20 mL) (Aldrich) was added a few drops of DMF (0.05 mL). The reaction mixture was then heated with stirring at 90° C. for 3 hours. The solvents were evaporated and the residue was dried in vacuo. The residue was dissolved in 2-propanol (30 mL), then 3-bromoaniline (0.69 g, 3.98 mmol) (Aldrich) was added. The reaction mixture was heated at 110° C. for 3 hours. The solvents were removed and the residue was purified by chromatography using EtOAc/CH₂Cl₂/NEt₃ (1:1:0.05) as eluent to give the desired (3-bromo-phenyl)-(6,7-dimethoxy-5-nitro-quinazolin-4-yl)-amine as a yellow solid. (Yield 1.2 g, 74%).

Step B: N4-(3-Bromo-phenyl)-6,7-dimethoxy-quinazoline-4,5-diamine

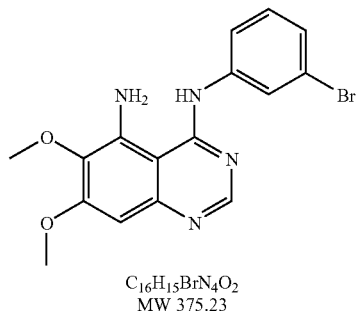

C₁₆H₁₅BrN₄O₂
MW 375.23

To a solution of (3-bromo-phenyl)-(6,7-dimethoxy-5-nitro-quinazolin-4-yl)-amine (0.2 g, 0.49 mmol) (from Example 6, Step A, supra) and NH₄Cl (0.26 g, 4.94 mmol) in a mixture of MeOH, H₂O and CHCl₃ (30 mL, 6:1:1) was added Zn powder (0.64 g, 9.87 mmol). The reaction mixture was stirred at room temperature for 3 hours. The mixture was then filtered, the filtrate was concentrated and then extracted with chloroform (100 mL). The organic layer was separated, dried over Na₂SO₄, and concentrated. This residue was purified by chromatography using EtOAc/CH₂Cl₂/NEt₃ (1:1:0.05) as eluent to give the desired N4-(3-bromo-phenyl)-6,7-dimethoxy-quinazoline-4,5-diamine as a yellow gum. (Yield 0.1 g, 54%).

Step C: 3-(3-Bromo-phenyl)-8,9-dimethoxy-3H-1,3,4,6-tetraaza-phenalene

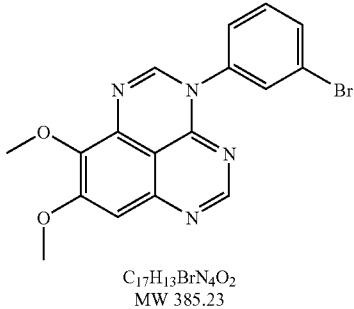

C₁₇H₁₃BrN₄O₂
MW 385.23

A solution of N4-(3-bromo-phenyl)-6,7-dimethoxy-quinazoline-4,5-diamine (100 mg, 0.27 mmol) (from Example 6, Step B supra) in formic acid (5 mL) was heated at 110° C. for 2 hours. Aqueous NaOH solution was added to the reaction mixture to a pH 10–12. The solution was diluted with chloroform (100 mL). The organic layer was separated, dried over Na₂SO₄, and concentrated. This residue was purified by chromatography using EtOAc/Et₃N (1:0.04) as eluent to give the desired 3-(3-bromo-phenyl)-8,9-dimethoxy-3H-1,3,4,6-tetraaza-phenalene as a brown solid. (Yield 86 mg, 83%).

Example 7

3-(3-Bromo-phenyl)-8,9-dimethoxy-1H,3H-1,3,4,6-tetraaza-phenalen-2-one

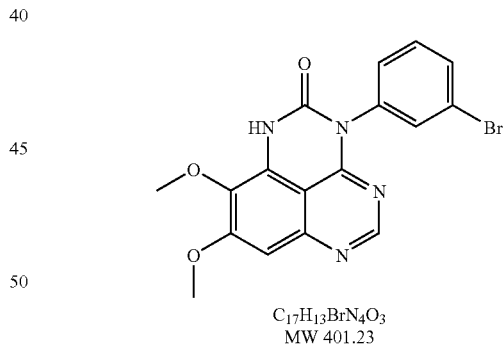

C₁₇H₁₃BrN₄O₃
MW 401.23

To a solution of N4-(3-bromo-phenyl)-6,7-dimethoxy-quinazoline-4,5-diamine (0.15 g, 0.40 mmol) (from Example 6, Step B, supra) in 1,2-dichloroethane (50 mL) was added 1,1'-carbonyldiimidazole (0.65 g, 4.0 mmol) (Aldrich). The reaction mixture was heated with stirring at 90° C. for 4 hours. The solvents were evaporated and the residue was purified by chromatography using EtOAc/CH₂Cl₂/Et₃N (1:1:0.05) as eluent to give the desired 3-(3-bromo-phenyl)-8,9-dimethoxy-1H,3H-1,3,4,6-tetraaza-phenalen-2-one as a brown solid. (Yield 0.12 g, 75%).

Example 8

3-(3-Bromo-phenyl)-8,9-dimethoxy-2-methyl-3H-1,3,4,6-tetraaza-phenalene

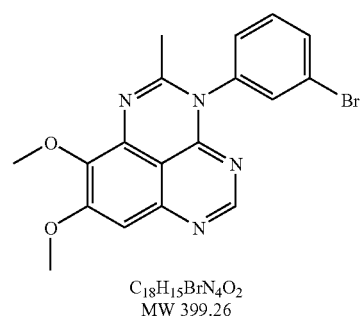

C$_{18}$H$_{15}$BrN$_4$O$_2$
MW 399.26

A solution of N4-(3-bromo-phenyl)-6,7-dimethoxy-quinazoline-4,5-diamine (120 mg, 0.32 mmol) (from Example 6, Step B, supra) in acetic anhydride (3 mL) was heated at 150° C. for 2 hours. Aqueous NaOH solution was added to the reaction mixture to a pH 10–12. The solution was extracted with chloroform (50 mL). The organic layer was separated, dried over Na$_2$SO$_4$, and concentrated. This residue was purified by chromatography using EtOAc/Et$_3$N (1:0.05) as eluent to give the desired 3-(3-bromo-phenyl)-8,9-dimethoxy-2-methyl-3H-1,3,4,6-tetraaza-phenalene as a brown solid. (Yield 60 mg, 47%).

Example 9

3-(3-Bromo-phenyl)-8,9-dimethoxy-1H,3H-1,3,4,6-tetraaza-phenalen-2-thione

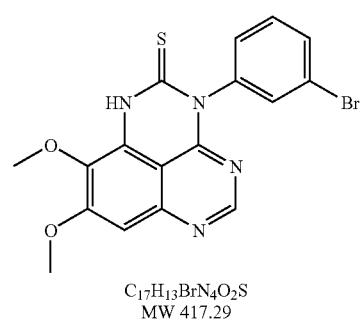

C$_{17}$H$_{13}$BrN$_4$O$_2$S
MW 417.29

To a solution of N4-(3-bromo-phenyl)-6,7-dimethoxy-quinazoline-4,5-diamine (80 mg, 0.21 mmol) (from Example 6, Step B, supra) in 1,2-dichloroethane (50 mL) was added 1,1'-thiocarbonyldiimidazole (0.38 g, 2.13 mmol) (Fluka). The reaction mixture was heated with stirring at 90° C. for 4 hours. The solvents were evaporated and the residue was purified by chromatography using EtOAc/CH$_2$Cl$_2$/Et$_3$N (1:2:0.05) as eluent to give the desired 3-(3-bromo-phenyl)-8,9-dimethoxy-1H,3H-1,3,4,6-tetraaza-phenalene-2-thione as a yellow solid. (Yield 80 mg, 91%).

Example 10

3-(3-Bromo-phenyl)-2-ethyl-8,9-dimethoxy-3H-1,3,4,6-tetraaza-phenalene

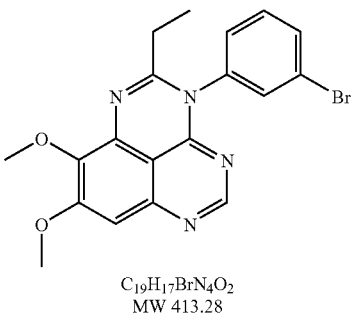

C$_{19}$H$_{17}$BrN$_4$O$_2$
MW 413.28

A solution of N4-(3-bromo-phenyl)-6,7-dimethoxy-quinazoline-4,5-diamine (120 mg, 0.32 mmol) (from Example 6, Step B, supra) in propionic anhydride (3 mL) (Aldrich) was heated at 170° C. for 2 hours. Aqueous NaOH solution was added to the reaction mixture to a pH 10–12. The solution was extracted with chloroform (50 mL). The organic layer was separated, dried over Na$_2$SO$_4$, and concentrated. This residue was purified by chromatography using EtOAc/Et$_3$N (1:0.05) as eluent to give the desired 3-(3-bromo-phenyl)-2-ethyl-8,9-dimethoxy-3H-1,3,4,6-tetraaza-phenalene as a brown solid. (Yield 50 mg, 38%).

Example 11

3-(3-Chloro-phenyl)-8,9-dimethoxy-1H,3H-1,3,4,6-tetraaza-phenalen-2-one

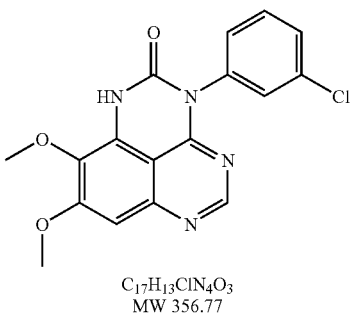

C$_{17}$H$_{13}$ClN$_4$O$_3$
MW 356.77

Step A: (3-Chloro-phenyl)-(6,7-dimethoxy-5-nitro-quinazolin-4-yl)-amine

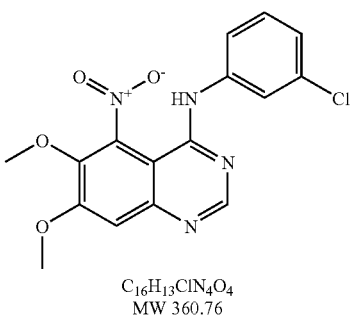

C$_{16}$H$_{13}$ClN$_4$O$_4$
MW 360.76

A solution of 6,7-dimethoxy-5-nitro-3H-quinazolin-4-one (0.5 g, 1.99 mmol) (from Example 1, Step A, supra) in SOCl₂ (20 mL) (Aldrich) and a few drops of DMF (0.05 mL) was heated with stirring at 90° C. for 3 hours. The solvents were then evaporated and the residue was dried in vacuo. The residue was dissolved in 2-propanol (30 mL), then 3-chloroaniline (0.25 g, 1.99 mmol) (Aldrich) was added. The reaction mixture was heated at 110° C. for 3 hours. The solvents were removed and the residue was purified by chromatography using EtOAc/CH₂Cl₂/NEt₃ (1:2:0.05) as eluent to give the desired (3-chloro-phenyl)-(6,7-dimethoxy-5-nitro-quinazolin-4-yl)-amine as a yellow solid. (Yield 0.4 g, 56%).

Step B: N4-(3-Chloro-phenyl)-6,7-dimethoxy-quinazoline-4,5-diamine

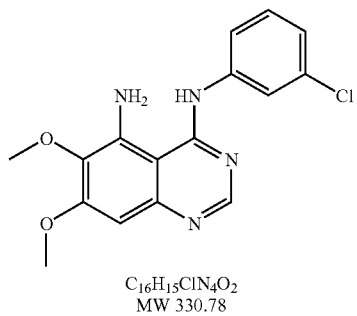

C₁₆H₁₅ClN₄O₂
MW 330.78

To a solution of (3-chloro-phenyl)-(6,7-dimethoxy-5-nitro-quinazolin-4-yl)-amine (0.2 g, 0.55 mmol) (from Example 11, Step A, supra) and NH₄Cl (0.24 g, 4.43 mmol) in a mixture of MeOH, H₂O and CHCl₃ (50 mL, 2:1:12), was added Zn powder (0.72 g, 11 mmol). The reaction mixture was stirred at room temperature for 3 hours. The mixture was then filtered. The filtrate was concentrated and then extracted with chloroform (100 mL). The organic layer was separated, dried over Na₂SO₄, and concentrated. The residue was purified by chromatography using EtOAc/CH₂Cl₂/NEt₃ (1:1:0.05) as eluent to give the desired N4-(3-chloro-phenyl)-6,7-dimethoxy-quinazoline-4,5-diamine as an orange gum. (Yield 0.1 g, 55%).

Step C: 3-(3-Chloro-phenyl)-8,9-dimethoxy-1H,3H-1,3,4,6-tetraaza-phenalen-2-one

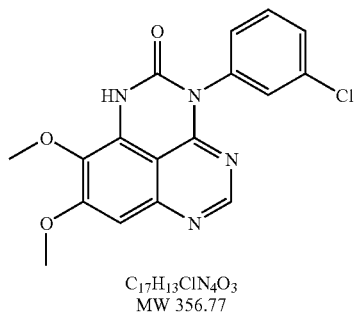

C₁₇H₁₃ClN₄O₃
MW 356.77

To a solution of N4-(3-chloro-phenyl)-6,7-dimethoxy-quinazoline-4,5-diamine (80 mg, 0.24 mmol) (from Example 11, Step B, supra) in 1,2-dichloroethane (30 mL) was added 1,1'-carbonyldiimidazole (0.2 g, 1.21 mmol) (Aldrich). The reaction mixture was heated with stirring at 90° C. for 4 hours. The solvents were evaporated and the residue was purified by chromatography using EtOAc/CH₂Cl₂/Et₃N (1:1:0.05) as eluent to give the desired 3-(3-chloro-phenyl)-8,9-dimethoxy-1H,3H-1,3,4,6-tetraaza-phenalen-2-one as a brown solid. (Yield 50 mg, 58%).

Example 12

3-(3-Chloro-phenyl)-8,9-dimethoxy-2-methyl-3H-1,3,4,6-tetraaza-phenalene

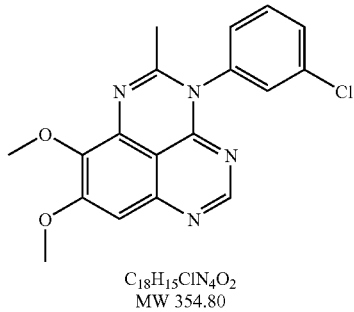

C₁₈H₁₅ClN₄O₂
MW 354.80

A solution of N4-(3-chloro-phenyl)-6,7-dimethoxy-quinazoline-4,5-diamine (0.2 g, 0.60 mmol) (from Example 11, Step B supra) in acetic anhydride (3 mL) was heated at 150° C. for 2 hours. Aqueous NaOH solution was added to the reaction mixture to a pH 10–12. The solution was extracted with chloroform (50 mL). The organic layer was separated, dried over Na₂SO₄, and concentrated. The residue was purified by chromatography using EtOAc/CH₂Cl₂/Et₃N (1:1:0.05) as eluent to give the desired 3-(3-chloro-phenyl)-8,9-dimethoxy-2-methyl-3H-1,3,4,6-tetraaza-phenalene as a yellow solid. (Yield 90 mg, 42%).

Example 13

3-(4-Chloro-phenyl)-8,9-dimethoxy-3H-1,3,4,6-tetraaza-phenalene

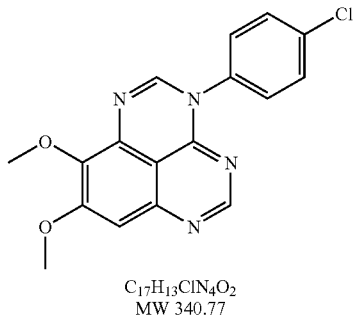

C₁₇H₁₃ClN₄O₂
MW 340.77

Step A: (4-Chloro-phenyl)-(6,7-dimethoxy-5-nitro-quinazolin-4-yl)-amine

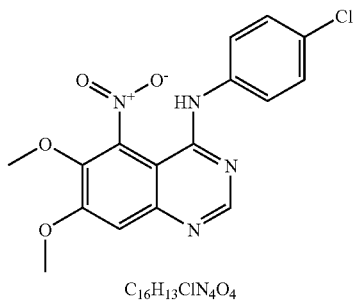

C₁₆H₁₃ClN₄O₄
MW 360.76

To a solution of 6,7-dimethoxy-5-nitro-3H-quinazolin-4-one (0.5 g, 1.99 mmol) (from Example 1, Step A, supra) in SOCl$_2$ (20 mL) (Aldrich) was added a few drops of DMF (0.05 mL). The reaction mixture was then heated with stirring at 90° C. for 3 hours. The solvents were evaporated and the residue was dried in vacuo. This residue was dissolved in 2-propanol (30 mL), then 4-chloroaniline (0.25 g, 1.99 mmol) (Aldrich) was added. The reaction mixture was heated at 110° C. for 3 hours. The solvents were removed and the residue was purified by chromatography using EtOAc/CH$_2$Cl$_2$/NEt$_3$ (1:2:0.05) as eluent to give the desired (4-chloro-phenyl)-(6,7-dimethoxy-5-nitro-quinazolin-4-yl)-amine as a yellow solid. (Yield 0.5 g, 70%).

Step B: N4-(4-Chloro-phenyl)-6,7-dimethoxy-quinazoline-4,5-diamine

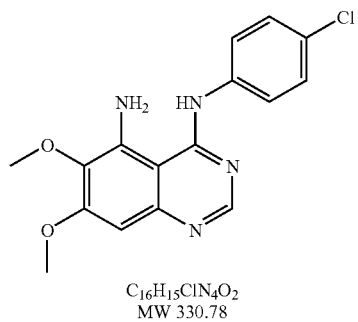

C$_{16}$H$_{15}$ClN$_4$O$_2$
MW 330.78

To a solution of (4-chloro-phenyl)-(6,7-dimethoxy-5-nitro-quinazolin-4-yl)-amine (0.2 g, 0.55 mmol) (from Example 13, Step A, supra) and NH$_4$Cl (0.24 g, 4.43 mmol) in a mixture of MeOH, H$_2$O and CHCl$_3$ (50 mL, 2:1:12) was added Zn powder (0.72 g, 11 mmol). The reaction mixture was stirred at room temperature for 3 hours. The mixture was then filtered, the filtrate was concentrated and then extracted with chloroform (100 mL). The organic layer was separated, dried over Na$_2$SO$_4$, and concentrated. The residue was purified by chromatography using EtOAc/CH$_2$Cl$_2$/NEt$_3$ (1:1:0.05) as eluent to give the desired N4-(4-chloro-phenyl)-6,7-dimethoxy-quinazoline-4,5-diamine as a pale yellow gum. (Yield 0.16 g, 88%).

Step C: 3-(4-Chloro-phenyl)-8,9-dimethoxy-3H-1,3,4,6-tetraaza-phenalene

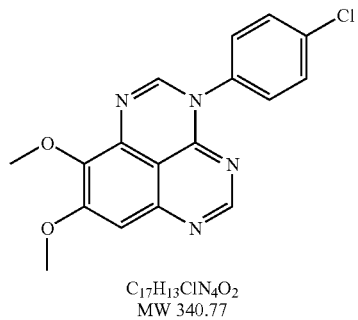

C$_{17}$H$_{13}$ClN$_4$O$_2$
MW 340.77

A solution of N4-(4-chloro-phenyl)-6,7-dimethoxy-quinazoline-4,5-diamine (160 mg, 0.48 mmol) (from Example 13, Step B, supra) in formic acid (2 mL) was heated at 110° C. for 2 hours. Aqueous NaOH solution was added to the reaction mixture to a pH 10–12. The solution was diluted with chloroform (100 mL). The organic layer was separated, dried over Na$_2$SO$_4$, and concentrated. This residue was purified by chromatography using EtOAc/Et$_3$N (1:0.05) as eluent to give the desired 3-(4-chloro-phenyl)-8,9-dimethoxy-3H-1,3,4,6-tetraaza-phenalene as an off white solid. (Yield 96 mg, 59%).

Example 14

3-(4-Chloro-phenyl)-8,9-dimethoxy-1H,3H-1,3,4,6-tetraaza-phenalen-2-thione

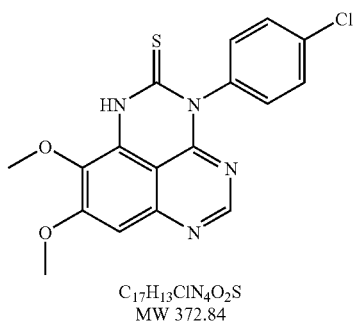

C$_{17}$H$_{13}$ClN$_4$O$_2$S
MW 372.84

To a solution of N4-(4-chloro-phenyl)-6,7-dimethoxy-quinazoline-4,5-diamine (120 mg, 0.36 mmol) (from Example 13, Step B, supra) in 1,2-dichloroethane (30 mL) was added 1,1'-thiocarbonyldiimidazole (0.65 g, 3.63 mmol) (Aldrich). The reaction mixture was heated with stirring at 90° C. for 4 hours. The solvents were evaporated and the residue was purified by chromatography using EtOAc/CH$_2$Cl$_2$/Et$_3$N (1:3:0.05) as eluent to give the desired 3-(4-chloro-phenyl)-8,9-dimethoxy-1H,3H-1,3,4,6-tetraaza-phenalene-2-thione as a yellow solid. (Yield 110 mg, 82%).

Example 15

7,8-Dimethoxy-5-methyl-4-phenyl-4H-1,3,4-triaza-phenalene

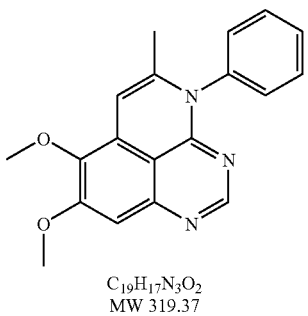

C$_{19}$H$_{17}$N$_3$O$_2$
MW 319.37

Step A: 6-Acetoxy-7-methoxy-4-phenylamino-quinazoline

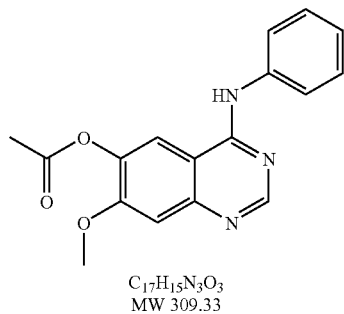

C$_{17}$H$_{15}$N$_3$O$_3$
MW 309.33

6-Acetoxy-7-methoxy-quinazolin-4-one (RO0505111-000) was synthesized according to the literature procedure of Gibson, K. H. et al. *Bioorganic & Medicinal Chemistry Letters,* 1997, 7(21), 2723–2728. To a solution of 6-acetoxy-7-methoxy-quinazolin-4-one (RO0505111-000) (1.2 g, 5.13 mmol) in SOCl$_2$ (30 mL) Aldrich) was added a few drops of DMF (0.1 mL). The reaction mixture was then heated with stirring at 100° C. for 3 hours. The solvents were evaporated and the residue was dried in vacuo. The residue was dissolved in 2-propanol (30 mL), then aniline (0.47 mL, 5.13 mmol) (Aldrich) was added. The reaction mixture was heated at 110° C. for 3 hours, then cooled to room temperature and filtered. The precipitate was collected and dried in vacuo to give 6-acetoxy-7-methoxy-4-phenylamino-quinazoline as a white solid. (Yield 1.0 g, 63%).

Step B: 7-Methoxy-4-phenylamino-quinazolin-6-ol

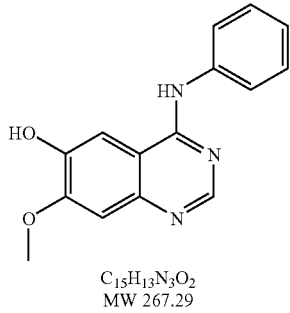

C$_{15}$H$_{13}$N$_3$O$_2$
MW 267.29

To a solution of 6-acetoxy-7-methoxy-4-phenylamino-quinazoline (1.01 g, 3.27 mmol) (from Example 15, Step A, supra) in MeOH (30 mL) was added an aqueous solution of NH$_4$OH (29%, 2.0 g, 31.4 mmol). The reaction mixture was stirred at room temperature for 18 hours, and then heated at 100° C. for 1.5 hours. The mixture was then cooled to room temperature and filtered. The precipitate was collected and dried in vacuo to give the desired 7-methoxy-4-phenylamino-quinazolin-6-ol as a white solid. (Yield 0.6 g, 69%).

Step C: (6-Allyloxy-7-methoxy-quinazolin-4-yl)-phenylamine

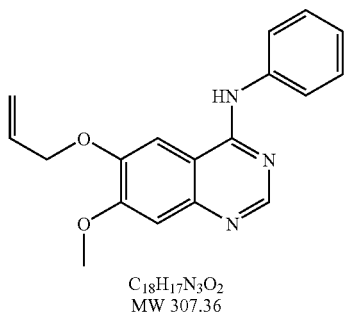

C$_{18}$H$_{17}$N$_3$O$_2$
MW 307.36

To a solution of 7-methoxy-4-phenylamino-quinazolin-6-ol (0.56 g, 2.1 mmol) (from Example 15, Step B, supra) in acetone (50 mL) was added K$_2$CO$_3$ (1.45 g, 10 mmol), and allyl bromide (0.2 mL, 2.3 mmol) (Aldrich). The reaction mixture was heated with stirring at 90° C. for 4 hours. The mixture was cooled to room temperature, filtered and the filtrate was concentrated. The residue was purified by chromatography using EtOAc/CH$_2$Cl$_2$/Et$_3$N (1:4:0.04) as eluent to give the desired (6-allyloxy-7-methoxy-quinazolin-4-yl)-phenyl-amine as a yellow solid. (Yield 0.6 g, 93%).

Step D: 5-Allyl-7-methoxy-4-phenylamino-quinazolin-6-ol

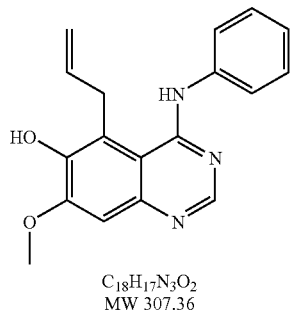

C$_{18}$H$_{17}$N$_3$O$_2$
MW 307.36

A solution of (6-allyloxy-7-methoxy-quinazolin-4-yl)-phenyl-amine (0.30 g, 0.98 mmol) (from Example 15, Step C, supra) in o-xylem (50 mL) was heated at 150° C. for 7 hours. At the end of this period, TLC analysis indicated almost complete consumption of the starting material and the formation of the desired product as the major spot. The solvent was evaporated and the residue was purified by chromatography using EtOAc/Et$_3$N (1:0.04) as eluent to give the desired 5-allyl-7-methoxy-4-phenylamino-quinazolin-6-ol as an off white solid. (Yield 0.26 g, 87%).

Step E: (5-Allyl-6,7-dimethoxy-quinazolin-4-yl)-phenyl-amine

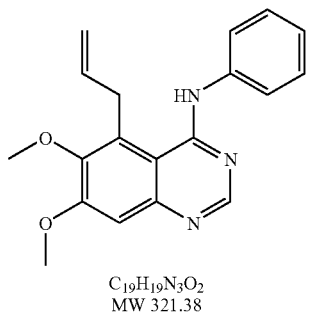

C$_{19}$H$_{19}$N$_3$O$_2$
MW 321.38

To a solution of 5-allyl-7-methoxy-4-phenylamino-quinazolin-6-ol (0.16 g, 0.524 mmol) (from Example 15, Step D, supra) in acetone (30 mL) was added K$_2$CO$_3$ (0.36 g, 2.62 mmol) and methyl iodide (0.15 g, 1.05 mmol) (Aldrich). The reaction mixture was heated with stirring at 90° C. for 4 hours. The mixture was cooled to room temperature, filtered and the filtrate was concentrated. The residue was purified by chromatography using EtOAc/CH$_2$Cl$_2$/Et$_3$N (1:5:0.05) as eluent to give the desired (5-allyl-6,7-dimethoxy-quinazolin-4-yl)-phenyl-amine as a pale yellow solid. (Yield 0.13 g, 77%).

Step F: 5-Iodomethyl-7,8-dimethoxy-4-phenyl-5,6-dihydro-4H-1,3,4-triaza-phenalene

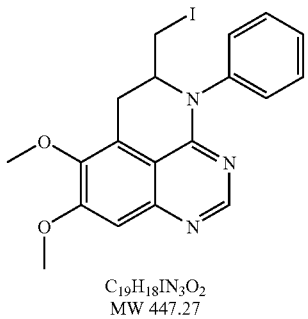

$C_{19}H_{18}IN_3O_2$
MW 447.27

To a solution of (5-allyl-6,7-dimethoxy-quinazolin-4-yl)-phenyl-amine (0.12 g, 0.37 mmol) (from Example 15, Step E, supra) in dichloromethane (20 mL) was added $I_2$ (0.24 g, 1.87 mmol). The reaction mixture was stirred at room temperature for 3 hours. The mixture was diluted with chloroform (100 mL), and washed with a saturated aqueous $Na_2SO_3$ solution. The organic layer was separated, dried over $Na_2SO_4$, and concentrated. The residue was purified by chromatography using $EtOAc/CH_2Cl_2/Et_3N$ (1:2:0.05) as eluent to give the desired 5-iodomethyl-7,8-dimethoxy-4-phenyl-5,6-dihydro-4H-1,3,4-triaza-phenalene as a pale yellow solid. (Yield 0.11 g, 66%).

Step G: 7,8-Dimethoxy-5-methyl-4-phenyl-4H-1,3,4-triaza-phenalene

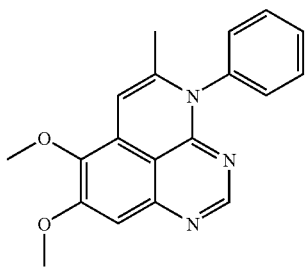

$C_{19}H_{17}N_3O_2$
MW 319.37

To a solution 5-iodomethyl-7,8-dimethoxy-4-phenyl-5,6-dihydro-4H-1,3,4-triaza-phenalene (0.1 g, 0.22 mmol) (from Example 15, Step F, supra) in toluene (20 mL) was added DBU (73 μL, 0.49 mmol) (Fluka). The reaction mixture was heated at 120° C. for 1 hour. The mixture was then diluted with chloroform (100 mL), and washed with $H_2O$. The organic layer was separated, dried over $Na_2SO_4$, and concentrated. The residue was purified by chromatography using $EtOAc/CH_2Cl_2/Et_3N$ (1:1:0.05) as eluent to give the desired 7,8-dimethoxy-5-methyl-4-phenyl-4H-1,3,4-triaza-phenalene as a pale yellow solid. (Yield 50 mg, 71%).

Example 16

4-(4-Chloro-phenyl)-7,8-dimethoxy-5-methyl-4H-1,3,4-triaza-phenalene

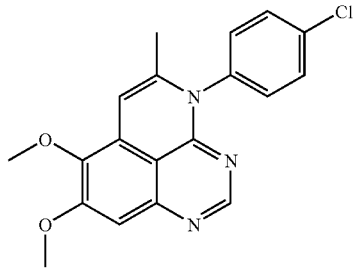

$C_{19}H_{16}ClN_3O_2$
MW 353.81

Step A: 6-Acetoxy-4-(4-chloro-phenylamino)-7-methoxy-quinazoline

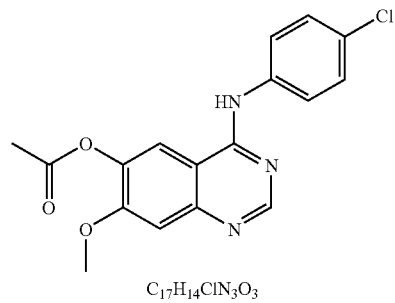

$C_{17}H_{14}ClN_3O_3$
MW 343.76

To a solution of 6-acetoxy-7-methoxy-quinazolin-4-one (RO0505111-000) (1.0 g, 4.26 mmol) (from Example 15, Step A, supra) in $SOCl_2$ (12.5 mL) (Aldrich) was added a few drops of DMF (0.1 mL). The reaction mixture was then heated with stirring at 100° C. for 3 hours. The solvents were evaporated and the residue was dried in vacuo. The residue was dissolved in 2-propanol (20 mL), then 4-chloroaniline (0.6 g, 4.69 mmol) (Fluka) was added. The reaction mixture was heated at 110° C. for 3 hours. The reaction mixture was cooled to room temperature and filtered. The precipitate was collected and dried in vacuo to give 6-acetoxy-4-(4-chloro-phenylamino)-7-methoxy-quinazoline as a gray solid. (Yield 1.45 g, 99%).

Step B: 4-(4-Chloro-phenylamino)-7-methoxy-quinazolin-6-ol

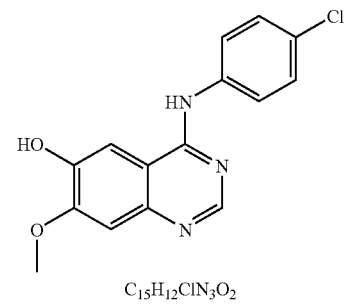

$C_{15}H_{12}ClN_3O_2$
MW 301.73

To a solution of 6-acetoxy-4-(4-chloro-phenylamino)-7-methoxy-quinazoline (1.4 g, 4.07 mmol) (from Example 16, Step A, supra) in MeOH (35 mL) was added an aqueous solution of NH$_4$OH (29%, 0.82 mL, 12.2 mmol). The reaction mixture was stirred at room temperature for 18 hours, then heated at 100° C. for 1.5 hours. The mixture was then cooled to room temperature and filtered. The precipitate was collected and dried in vacuo to give the desired 4-(4-chloro-phenylamino)-7-methoxy-quinazolin-6-ol as a gray solid. (Yield 0.67 g, 55%).

Step C: (6-Allyloxy-7-methoxy-quinazolin-4-yl)-(4-chloro-phenyl)-amine

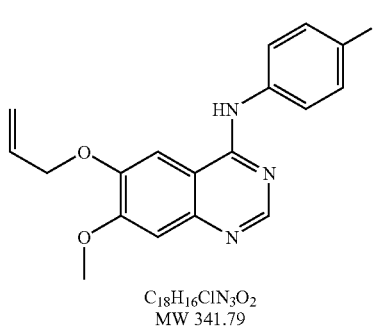

C$_{18}$H$_{16}$ClN$_3$O$_2$
MW 341.79

To a solution of 4-(4-chloro-phenylamino)-7-methoxy-quinazolin-6-ol (0.61 g, 2.02 mmol) (from Example 16, Step B, supra) in acetone (50 mL) was added K$_2$CO$_3$ (0.84 g, 6.06 mmol), and allyl bromide (0.52 mL, 6.06 mmol) (Aldrich). The reaction mixture was heated with stirring at 90° C. for 4 hours. The mixture was cooled to room temperature, filtered and the filtrate was concentrated. The residue was purified by chromatography using EtOAc/CH$_2$Cl$_2$/Et$_3$N (1:1:0.01) as eluent to give the desired (6-allyloxy-7-methoxy-quinazolin-4-yl)-(4-chloro-phenyl)-amine as a white solid. (Yield 0.5 g, 72%).

Step D: 5-Allyl-4-(4-chloro-phenylamino)-7-methoxy-quinazolin-6-ol

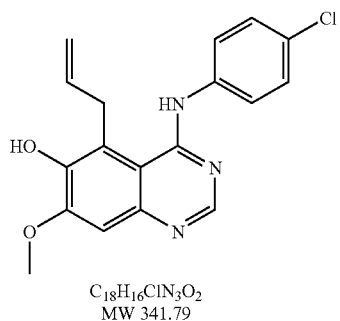

C$_{18}$H$_{16}$ClN$_3$O$_2$
MW 341.79

A solution of (6-allyloxy-7-methoxy-quinazolin-4-yl)-(4-chloro-phenyl)-amine (0.50 g, 1.46 mmol) (from Example 16, Step C, supra) in o-xylene (50 mL) was heated at 150° C. for 7 hours. At the end of this period, TLC analysis indicated almost complete consumption of the starting material and the formation of desired product as the major spot. The solvent was evaporated and the residue was purified by chromatography using EtOAc/Et$_3$N (1:0.04) as eluent to give the desired 5-allyl-4-(4-chloro-phenylamino)-7-methoxy-quinazolin-6-ol as an off white solid. (Yield 0.4 g, 80%).

Step E: (5-Allyl-6,7-dimethoxy-quinazolin-4-yl)-(4-chloro-phenyl)-amine

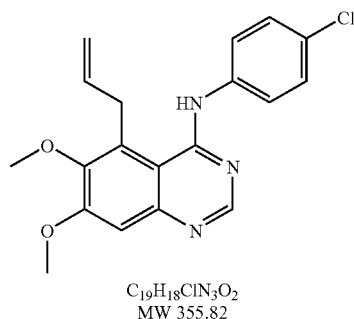

C$_{19}$H$_{18}$ClN$_3$O$_2$
MW 355.82

To a solution of 5-allyl-4-(4-chloro-phenylamino)-7-methoxy-quinazolin-6-ol (0.45 g, 1.32 mmol) (from Example 16, Step D, supra) in acetone (30 mL) was added K$_2$CO$_3$ (0.36 g, 2.6 mmol) and methyl iodide (0.75 g, 5.3 mmol) (Aldrich). The reaction mixture was heated with stirring at 90° C. for 4 hours. The mixture was cooled to room temperature, filtered and the filtrate was concentrated. The residue was purified by chromatography using EtOAc/CH$_2$Cl$_2$/Et$_3$N (1:2:0.01) as eluent to give the desired (5-allyl-6,7-dimethoxy-quinazolin-4-yl)-(4-chloro-phenyl)-amine as a white solid. (Yield 0.3 g, 84%).

Step F: 4-(4-Chloro-phenyl)-5-iodomethyl-7,8-dimethoxy-5,6-dihydro-4H-1,3,4-triaza-phenalene

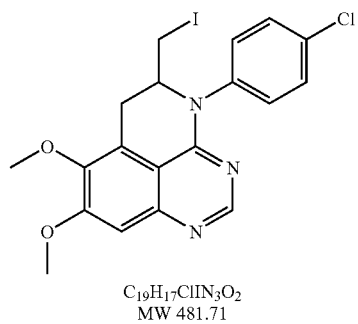

C$_{19}$H$_{17}$ClIN$_3$O$_2$
MW 481.71

To a solution of (5-allyl-6,7-dimethoxy-quinazolin-4-yl)-(4-chloro-phenyl)-amine (0.3 g, 0.85 mmol) (from Example 16, Step E, supra) in dichloromethane (50 mL) was added I$_2$ (0.53 g, 4.2 mmol). The reaction mixture was stirred at room temperature for 3 hours. The mixture was diluted with chloroform (100 mL), and washed with a saturated aqueous Na$_2$SO$_3$ solution. The organic layer was separated, dried over Na$_2$SO$_4$, and concentrated. The residue was purified by chromatography using EtOAc/CH$_2$Cl$_2$/Et$_3$N (2:1:0.01) as eluent to give the desired 4-(4-chloro-phenyl)-5-iodomethyl-7,8-dimethoxy-5,6-dihydro-4H-1,3,4-triaza-phenalene as a white solid. (Yield 0.15 g, 37%).

Step G: 4-(4-Chloro-phenyl)-7,8-dimethoxy-5-methyl-4H-1,3,4-triaza-phenalene

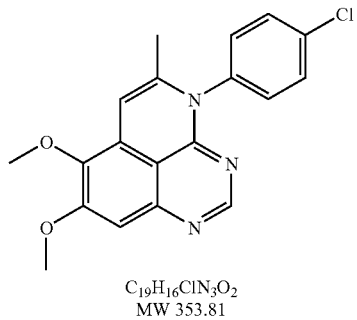

C$_{19}$H$_{16}$ClN$_3$O$_2$
MW 353.81

To a solution of 4-(4-chloro-phenyl)-5-iodomethyl-7,8-dimethoxy-5,6-dihydro-4H-1,3,4-triaza-phenal (0.15 g, 0.31 mmol) (from Example 16, Step F, supra) in toluene (50 mL) was added DBU (0.46 mL, 3.1 mmol) (Fluka). The reaction mixture was heated at 120° C. for 1 hour. The mixture was then diluted with chloroform (100 mL), and washed with H$_2$O. The organic layer was separated, dried over Na$_2$SO$_4$, and concentrated. The residue was purified by chromatography using EtOAc/CH$_2$Cl$_2$/Et$_3$N (1:1:0.05) as eluent to give the desired 4-(4-chloro-phenyl)-7,8-dimethoxy-5-methyl-4H-1,3,4-triaza-phenalene as a pale yellow solid. (Yield 0.1 g, 91%).

Example 17

4-(3-Bromo-phenyl)-7,8-dimethoxy-5-methyl-4H-1,3,4-triaza-phenalene

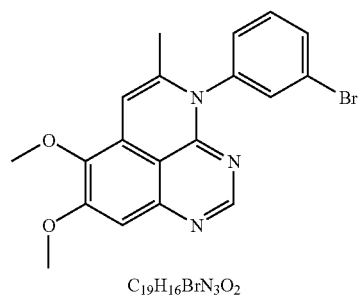

C$_{19}$H$_{16}$BrN$_3$O$_2$
MW 398.25

Step A: 6-Acetoxy-4-(3-bromo-phenylamino)-7-methoxy-quinazoline

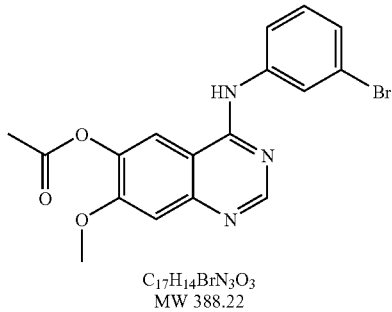

C$_{17}$H$_{14}$BrN$_3$O$_3$
MW 388.22

To a solution of 6-acetoxy-7-methoxy-quinazolin-4-one (RO0505111-000) (1.0 g, 4.26 mmol) (from Example 15, Step A, supra) in SOCl$_2$ (12.5 mL) (Aldrich) was added a few drops of DMF (0.1 mL). The reaction mixture was then heated with stirring at 100° C. for 3 hours. The solvents were evaporated and the residue was dried in vacuo. The residue was dissolved in 2-propanol (20 mL), then 3-bromoaniline (0.806 g, 4.69 mmol) (Aldrich) was added. The reaction mixture was heated at 110° C. for 3 hours. The reaction mixture was cooled to room temperature and filtered. The precipitate was collected and dried in vacuo to give 6-acetoxy-4-(3-bromo-phenylamino)-7-methoxy-quinazoline as a gray solid. (Yield 1.65 g, 100%).

Step B: 4-(3-Bromo-phenylamino)-7-methoxy-quinazolin-6-ol

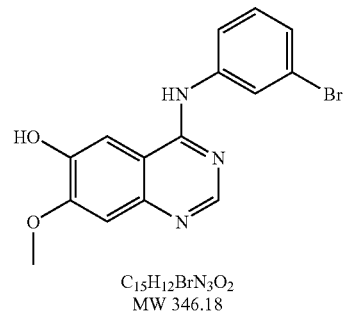

C$_{15}$H$_{12}$BrN$_3$O$_2$
MW 346.18

To a solution of 6-acetoxy-4-(3-bromo-phenylamino)-7-methoxy-quinazoline (1.59 g, 4.11 mmol) (from Example 17, Step A, supra) in MeOH (30 mL) was added an aqueous solution of NH$_4$OH (29%, 0.83 mL, 12.3 mmol). The reaction mixture was stirred at room temperature for 18 hours, then heated at 100° C. for 1.5 hours. The mixture was then cooled to room-temperature and filtered. The precipitate was collected and dried in vacuo to give the desired 4-(3-bromo-phenylamino)-7-methoxy-quinazolin-6-ol as a gray solid. (Yield 1.25 g, 88%).

Step C: (6-Allyloxy-7-methoxy-quinazolin-4-yl)-(3-bromo-phenyl)-amine

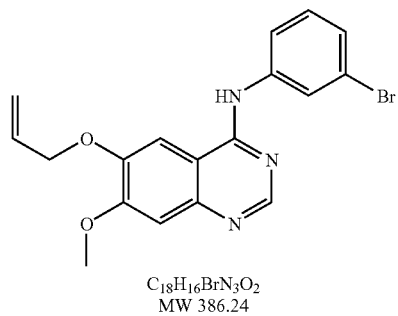

C$_{18}$H$_{16}$BrN$_3$O$_2$
MW 386.24

To a solution of 4-(3-bromo-phenylamino)-7-methoxy-quinazolin-6-ol (1.24 g, 3.58 mmol) (from Example 17, Step B, supra) in acetone (250 mL) was added K$_2$CO$_3$ (0.99 g, 7.16 mmol), and allyl bromide (1.55 mL, 17.9 mmol) (Aldrich). The reaction mixture was heated with stirring at 90° C. for 4 hours. The mixture was cooled to room temperature, filtered and the filtrate was concentrated. The residue was purified by chromatography using EtOAc/CH₂Cl₂/Et₃N (2:3:0.02) as eluent to give the desired (6-allyloxy-7-methoxy-quinazolin-4-yl)-(3-bromo-phenyl)-amine as a yellow oil. (Yield 0.55 g, 40%).

Step D: 5-Allyl-4-(3-bromo-phenylamino)-7-methoxy-quinazolin-6-ol

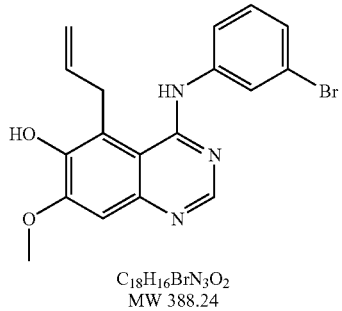

C$_{18}$H$_{16}$BrN$_3$O$_2$
MW 388.24

A solution of (6-allyloxy-7-methoxy-quinazolin-4-yl)-(3-bromo-phenyl)-amine (0.54 g, 1.39 mmol) (from Example 17, Step C, supra) in o-xylene (75 mL) was heated at 150° C. for 4.5 hours, during which time TLC analysis indicated almost complete consumption of the starting material and the formation of desired product as the major spot. The solution was concentrated and filtered. The solid was collected and dried in vacuo to give the desired 5-allyl-4-(3-bromo-phenylamino)-7-methoxy-quinazolin-6-ol as an off white solid. (Yield 0.33 g, 61%).

Step E: (5-Allyl-6,7-dimethoxy-quinazolin-4-yl)-(3-bromo-phenyl)-amine

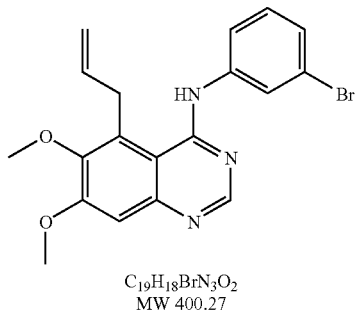

C$_{19}$H$_{18}$BrN$_3$O$_2$
MW 400.27

To a solution of 5-allyl-4-(3-bromo-phenylamino)-7-methoxy-quinazolin-6-ol (0.27 g, 0.7 mmol) (from Example 17, Step D, supra) in acetone (30 mL) was added K₂CO₃ (0.48 g, 3.5 mmol) and methyl iodide (0.4 g, 2.8 mmol) (Aldrich). The reaction mixture was heated with stirring at 90° C. for 4 hours. The mixture was cooled to room temperature, filtered, and the filtrate was concentrated. The residue was purified by chromatography using EtOAc/CH₂Cl₂/Et₃N (1:3:0.01) as eluent to give the desired (5-allyl-6,7-dimethoxy-quinazolin-4-yl)-(3-bromo-phenyl)-amine as a yellow solid. (Yield 0.14 g, 50%).

Step F: 4-(3-Bromo-phenyl)-5-iodomethyl-7,8-dimethoxy-5,6-dihydro-4H-1,3,4-triaza-phenalene

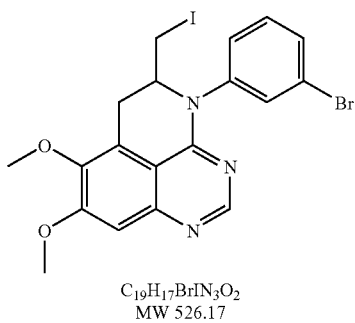

C$_{19}$H$_{17}$BrIN$_3$O$_2$
MW 526.17

To a solution of (5-allyl-6,7-dimethoxy-quinazolin-4-yl)-(3-bromo-phenyl)-amine (0.14 g, 0.35 mmol) (from Example 17, Step E, supra) in dichloromethane (20 mL) was added I₂ (0.23 g, 1.75 mmol). The reaction mixture was stirred at room temperature for 3 hours. The mixture was diluted with chloroform (100 mL) and washed with a saturated aqueous Na₂SO₃ solution. The organic layer was separated, dried over Na₂SO₄, and concentrated. The residue was purified by chromatography using EtOAc/CH₂Cl₂/Et₃N (1:2:0.01) as eluent to give the desired 4-(3-bromo-phenyl)-5-iodomethyl-7,8-dimethoxy-5,6-dihydro-4H-1,3,4-triaza-phenalene as a pale yellow foam. (Yield 0.12 g, 66%).

Step G: 4-(3-Bromo-phenyl)-7,8-dimethoxy-5-methyl-4H-1,3,4-triaza-phenalene

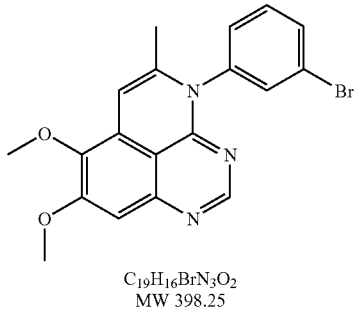

C$_{19}$H$_{16}$BrN$_3$O$_2$
MW 398.25

To a solution of 4-(3-bromo-phenyl)-5-iodomethyl-7,8-dimethoxy-5,6-dihydro-4H-1,3,4-triaza-phenale (0.12 g, 0.23 mmol) (from Example 17, Step F, supra) in toluene (20 mL) was added DBU (0.075 mL, 0.5 mmol) (Fluka). The reaction mixture was heated at 120° C. for 1 hour. The mixture was then diluted with chloroform (100 mL), and washed with H₂O. The organic layer was separated, dried over Na₂SO₄, and concentrated. The residue was purified by chromatography using EtOAc/CH₂Cl₂/Et₃N (1:2:0.05) as eluent to give the desired 4-(3-bromo-phenyl)-7,8-dimethoxy-5-methyl-4H-1,3,4-triaza-phenalene as a pale yellow solid. (Yield 0.09 g, 100%).

Example 18

4-(3-Chloro-4-fluoro-phenyl)-7,8-dimethoxy-5-methyl-4H-1,3,4-triaza-phenalene

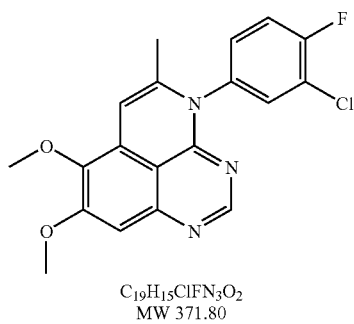

$C_{19}H_{15}ClFN_3O_2$
MW 371.80

Step A: 6-Acetoxy-4-(3-chloro-4-fluoro-phenylamino)-7-methoxy-quinazoline

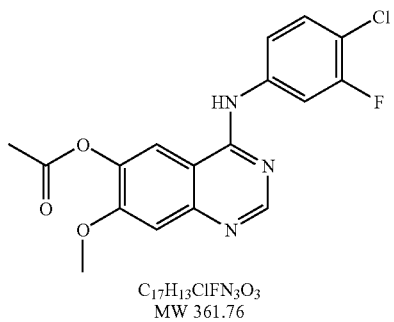

$C_{17}H_{13}ClFN_3O_3$
MW 361.76

To a solution of 6-acetoxy-7-methoxy-quinazolin-4-one (RO0505111-000) (1.0 g, 4.26 mmol) (from Example 15, Step A, supra) in SOCl$_2$ (12.5 mL) (Aldrich) were added a few drops of DMF (0.1 mL). The reaction mixture was then heated with stirring at 100° C. for 3 hours. The solvents were evaporated and the residue was dried in vacuo. The residue was dissolved in 2-propanol (20 mL), followed by addition of 4-chloro-3-fluoroaniline (0.682 g, 4.69 mmol) (Aldrich). The reaction mixture was heated at 110° C. for 3 hours. The reaction mixture was cooled to room temperature and filtered. The precipitate was collected and dried in vacuo to give 6-acetoxy-4-(3-chloro-4-fluoro-phenylamino)-7-methoxy-quinazoline as a gray solid. (Yield 1.54 g, 100%).

Step B: 4-(4-Chloro-4-fluoro-phenylamino)-7-methoxy-quinazolin-6-ol

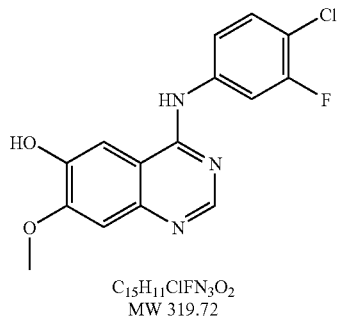

$C_{15}H_{11}ClFN_3O_2$
MW 319.72

To a solution of 6-acetoxy-4-(3-chloro-4-fluoro-phenylamino)-7-methoxy-quinazoline (1.54 g, 4.26 mmol) (from Example 18, Step A, supra) in MeOH (30 mL) was added an aqueous solution of NH$_4$OH (29%, 0.86 mL, 12.7 mmol). The reaction mixture was stirred at room temperature for 18 hours, then heated at 100° C. for 1.5 hours. The mixture was then cooled to room temperature and filtered. The precipitate was collected and dried in vacuo to give the desired 4-(3-chloro-4-fluoro-phenylamino)-7-methoxy-quinazolin-6-ol as a gray solid. (Yield 1.21 g, 89%).

Step C: (6-Allyloxy-7-methoxy-quinazolin-4-yl)-(3-chloro-4-fluoro-phenyl)-amine

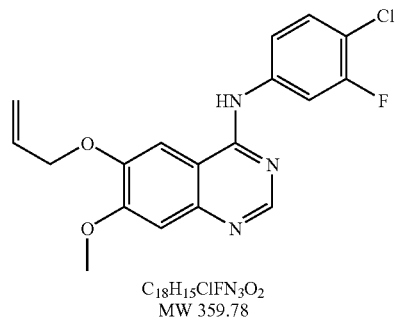

$C_{18}H_{15}ClFN_3O_2$
MW 359.78

To a solution of 4-(3-chloro-4-fluoro-phenylamino)-7-methoxy-quinazolin-6-ol (0.70 g, 2.18 mmol) (from Example 18, Step B, supra) in acetone (140 mL) was added K$_2$CO$_3$ (0.61 g, 10.9 mmol) and allyl bromide (0.94 mL, 10.9 mmol) (Aldrich). The reaction mixture was heated with stirring at 90° C. for 4 hours. The mixture was cooled to room temperature, filtered, and the filtrate was concentrated. The residue was purified by chromatography using EtOAc/CH$_2$C$_2$/Et$_3$N (1:1:0.02) as eluent to give the desired (6-allyloxy-7-methoxy-quinazolin-4-yl)-(3-chloro-4-fluoro-phenyl)-amine as an off white solid. (Yield 0.64 g, 82%).

Step D: 5-Allyl-4-(3-chloro-4-fluoro-phenylamino)-7-methoxy-quinazolin-6-ol

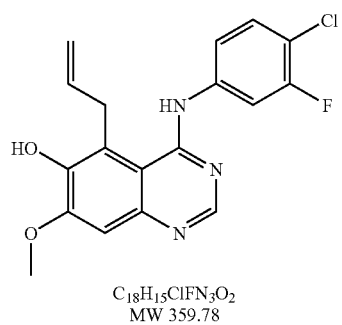

$C_{18}H_{15}ClFN_3O_2$
MW 359.78

A solution of (6-allyloxy-7-methoxy-quinazolin-4-yl)-(3-chloro-4-fluoro-phenyl)-amine (0.92 g, 2.55 mmol) (from Example 18, Step C, supra) in o-xylene (150 mL) was heated at 150° C. for 7 hours. At the end of this period, TLC analysis indicated almost complete consumption of the starting material and the formation of desired product as the major spot. The solution was concentrated and filtered. The solid was collected and dried in vacuo to give the desired 5-allyl-4-(3-chloro-4-fluoro-phenylamino)-7-methoxy-quinazolin-6-ol as an off white solid. (Yield 0.65 g, 71%).

Step E: (5-Allyl-6,7-dimethoxy-quinazolin-4-yl)-(3-chloro-4-fluoro-phenyl)-amine

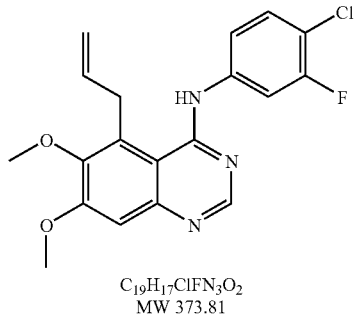

$C_{19}H_{17}ClFN_3O_2$
MW 373.81

To a solution of 5-allyl-4-(3-chloro-4-fluoro-phenylamino)-7-methoxy-quinazolin-6-ol (0.59 g, 1.63 mmol) (from Example 18, Step D, supra) in acetone (175 mL) was added $K_2CO_3$ (0.68 g, 4.91 mmol) and methyl iodide (2.32 g, 16.4 mmol) (Aldrich). The reaction mixture was heated with stirring at 90° C. for 3 hours. The mixture was cooled to room temperature, filtered and the filtrate was concentrated. The residue was purified by chromatography using $EtOAc/CH_2Cl_2/Et_3N$ (1:3:0.01) as eluent to give the desired (5-allyl-6,7-dimethoxy-quinazolin-4-yl)-(3-chloro-4-fluoro-phenyl)-amine as an off white solid. (Yield 0.29 g, 48%).

Step F: 4-(3-Chloro-4-fluoro-phenyl)-5-iodomethyl-7,8-dimethoxy-5,6-dihydro-4H-1,3,4-triaza-phenalene

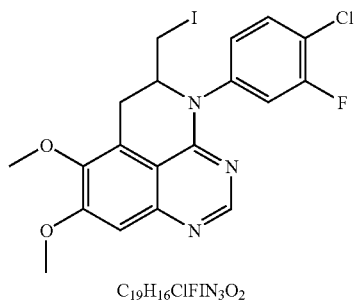

$C_{19}H_{16}ClFIN_3O_2$
MW 499.70

To a solution of (5-allyl-6,7-dimethoxy-quinazolin-4-yl)-(3-chloro-4-fluoro-phenyl)-amine (0.102 g, 0.27 mmol) (from Example 18, Step E, supra) in dichloromethane (20 mL) was added $I_2$ (0.69 g, 2.7 mmol). The reaction mixture was stirred at room temperature for 2 hours. The mixture was diluted with chloroform (100 mL) and washed with a saturated aqueous $Na_2SO_3$ solution. The organic layer was separated, dried over $Na_2SO_4$, and concentrated to give the desired 4-(3-chloro-4-fluoro-phenyl)-5-iodomethyl-7,8-dimethoxy-5,6-dihydro-4H-1,3,4-triaza-phenalene as a yellow foam. (Yield 0.134 g, 99%).

Step G: 4-(3-Bromo-phenyl)-7,8-dimethoxy-5-methyl-4H-1,3,4-triaza-phenalene

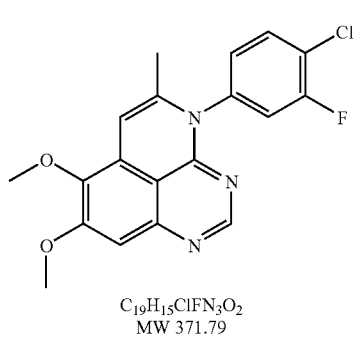

$C_{19}H_{15}ClFN_3O_2$
MW 371.79

To a solution of 4-(3-chloro-4-fluoro-phenyl)-5-iodomethyl-7,8-dimethoxy-5,6-dihydro-4H-1,3,4-triaza-phenalene (0.125 g, 0.25 mmol) (from Example 18, Step F, supra) in toluene (25 mL) was added DBU (0.37 mL, 2.5 mmol) (Fluka). The reaction mixture was heated at 120° C. for 1 hours. The mixture was then diluted with chloroform (100 mL) and washed with $H_2O$. The organic layer was separated, dried over $Na_2SO_4$, and concentrated. The residue was purified by chromatography using $EtOAc/CH_2Cl_2/Et_3N$ (3:1:0.05) as eluent to give the desired 4-(3-chloro-4-fluoro-phenyl)-7,8-dimethoxy-5-methyl-4H-1,3,4-triaza-phenalene as a white solid. (Yield 0.093 g, 100%).

Example 19

4-(4-Bromo-2-fluoro-phenyl)-7,8-dimethoxy-5-methyl-4H-1,3,4-triaza-phenalene

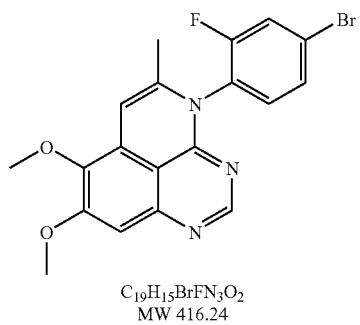

$C_{19}H_{15}BrFN_3O_2$
MW 416.24

Step A: 6-Acetoxy-4-(4-bromo-2-fluoro-phenylamino)-7-methoxy-quinazoline

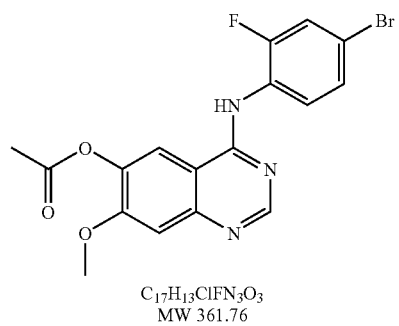

$C_{17}H_{13}ClFN_3O_3$
MW 361.76

To a solution of 6-acetoxy-7-methoxy-quinazolin-4-one (RO0505111-000) (1.0 g, 4.26 mmol) (from Example 15, Step A, supra) in $SOCl_2$ (12.5 mL) (Aldrich) were added a few drops of DMF (0.1 mL). The reaction mixture was then heated with stirring at 100° C. for 3 hours. The solvents were evaporated and the residue was dried in vacuo. The residue was dissolved in 2-propanol (20 mL), then 4-bromo-2-fluoroaniline (0.891 g, 4.69 mmol) (Aldrich) was added. The reaction mixture was heated at 110° C. for 3 hours. The reaction mixture was cooled to room temperature and filtered. The precipitate was collected and dried in vacuo to give 6-acetoxy-4-(4-bromo-2-fluoro-phenylamino)-7-methoxy-quinazoline as a gray solid. (Yield 1.42 g, 82%).

Step B: 4-(4-Bromo-2-fluoro-phenylamino)-7-methoxy-quinazolin-6-ol

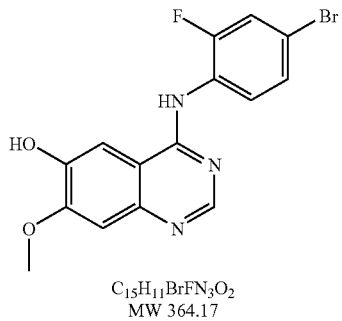

C$_{15}$H$_{11}$BrFN$_3$O$_2$
MW 364.17

To a solution of 6-acetoxy-4-(4-bromo-2-fluoro-phenylamino)-7-methoxy-quinazoline (1.36 g, 3.34 mmol) (from Example 19, Step A, supra) in MeOH (30 mL) was added an aqueous solution of NH$_4$OH (29%, 0.68 mL, 10 mmol). The reaction mixture was stirred at room temperature for 18 hours, then heated at 100° C. for 1.5 hours. The mixture was then cooled to room temperature and filtered. The precipitate was collected and dried in vacuo to give the desired 4-(4-bromo-2-fluoro-phenylamino)-7-methoxy-quinazolin-6-ol as a gray solid. (Yield 0.93 g, 77%).

Step C: (6-Allyloxy-7-methoxy-quinazolin-4-yl)-(4-bromo-2-fluoro-phenyl)-amine

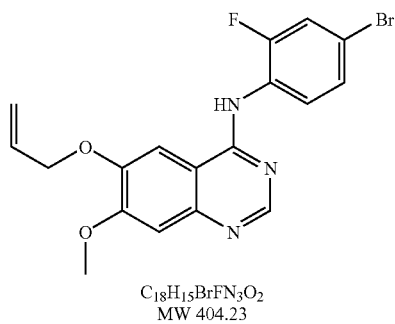

C$_{18}$H$_{15}$BrFN$_3$O$_2$
MW 404.23

To a solution of 4-(4-bromo-2-fluoro-phenylamino)-7-methoxy-quinazolin-6-ol (0.50 g, 1.37 mmol) (from Example 19, Step B, supra) in acetone (100 mL) was added K$_2$CO$_3$ (0.38 g, 2.74 mmol), and allyl bromide (0.59 mL, 6.86 mmol) (Aldrich). The reaction mixture was heated with stirring at 90° C. for 2 hours. The mixture was cooled to room temperature, filtered, and the filtrate was concentrated. The residue was purified by chromatography using EtOAc/CH$_2$Cl$_2$/Et$_3$N (1:1:0.02) as eluent to give the desired (6-allyloxy-7-methoxy-quinazolin-4-yl-(4-bromo-2-fluoro-phenyl)-amine as a pale yellow solid. (Yield 0.52 g, 95%).

Step D: 5-Allyl-4-(4-bromo-2-fluoro-phenylamino)-7-methoxy-quinazolin-6-ol

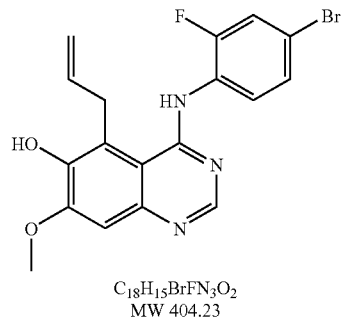

C$_{18}$H$_{15}$BrFN$_3$O$_2$
MW 404.23

A solution of (6-allyloxy-7-methoxy-quinazolin-4-yl)-(4-bromo-2-fluoro-phenyl)-amine (0.46 g, 1.13 mmol) (from Example 19, Step C, supra) in o-xylene (75 mL) was heated at 150° C. for 4 hours. At the end of this period, TLC analysis indicated almost complete consumption of the starting material and the formation of desired product as the major spot. The solution was concentrated to a small volume and filtered. The solid was collected and dried in vacuo to give the desired 5-allyl-4-(4-bromo-2-fluoro-phenylamino)-7-methoxy-quinazolin-6-ol as an off white solid. (Yield 0.35 g, 76%).

Step E: (5-Allyl-6,7-dimethoxy-quinazolin-4-yl)-(4-bromo-2-fluoro-phenyl)-amine

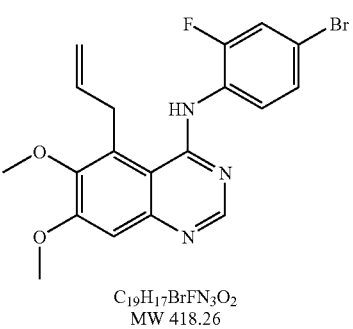

C$_{19}$H$_{17}$BrFN$_3$O$_2$
MW 418.26

To a solution of 5-allyl-4-(4-bromo-2-fluoro-phenylamino)-7-methoxy-quinazolin-6-ol (0.34 g, 0.84 mmol) (from Example 19, Step D, supra) in acetone (100 mL) was added K$_2$CO$_3$ (0.35 g, 2.52 mmol) and methyl iodide (1.19 g, 8.41 mmol) (Aldrich). The reaction mixture was heated with stirring at 90° C. for 4.5 hours. The mixture was cooled to room temperature, filtered, and the filtrate was concentrated. The residue was purified by chromatography using EtOAc/CH$_2$Cl$_2$/Et$_3$N (1:4:0.01) as eluent to give the desired (5-allyl-6,7-dimethoxy-quinazolin-4-yl)-(4-bromo-2-fluoro-phenyl)-amine as a yellow solid. (Yield 0.33 g, 94%).

Step F: 4-(4-Bromo-2-fluoro-phenyl)-5-iodomethyl-7,8-dimethoxy-5,6-dihydro-4H-1,3, 4-triaza-phenalene

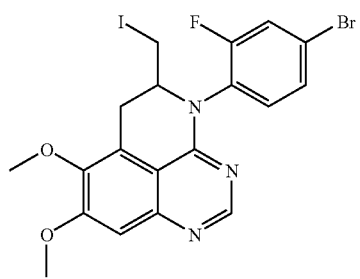

C$_{19}$H$_{16}$BrFIN$_3$O$_2$
MW 544.16

To a solution of (5-allyl-6,7-dimethoxy-quinazolin-4-yl)-(4-bromo-2-fluoro-phenyl)-amine (0.236 g, 0.564 mmol) (from Example 19, Step E, supra) in dichloromethane (30 mL) was added I$_2$ (1.43 g, 5.64 mmol). The reaction mixture was stirred at room temperature for 4 hours. The mixture was diluted with chloroform (100 mL), and washed with a saturated aqueous Na$_2$SO$_3$ solution. The organic layer was separated, dried over Na$_2$SO$_4$, and concentrated to give the desired 4-(4-bromo-2-fluoro-phenyl)-5-iodomethyl-7,8-dimethoxy-5,6-dihydro-4H-1,3,4-triaza-phenalene as an off white oil. (Yield 0.034 g, 11%).

Step G: 4-(4-Bromo-2-fluoro-phenyl)-7,8-dimethoxy-5-methyl-4H-1,3,4-triaza-phenalene

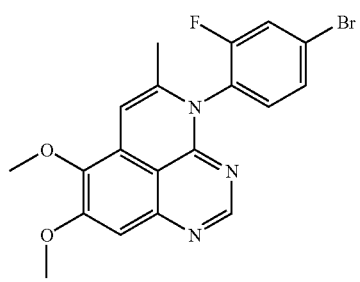

C$_{19}$H$_{15}$BrFN$_3$O$_2$
MW 416.24

To a solution of 4-(4-bromo-2-fluoro-phenyl)-5-iodomethyl-7,8-dimethoxy-5,6-dihydro-4H-1,3,4-triaza-phenalene (33 mg, 0.06 mmol) (from Example 19, Step F, supra) in toluene (7 mL) was added DBU (0.09 mL, 0.6 mmol) (Fluka). The reaction mixture was heated at 120° C. for 1 hour. The mixture was then diluted with chloroform (100 mL), and washed with H$_2$O. The organic layer was separated, dried over Na$_2$SO$_4$, and concentrated. The residue was purified by chromatography using EtOAc/CH$_2$Cl$_2$ /Et$_3$N (1:1:0.05) as eluent to give the desired 4-(4-bromo-2-fluoro-phenyl)-7,8-dimethoxy-5-methyl-4H-1,3,4-triaza-phenalene as a white solid. (Yield 0.027 g 100%).

Example 20

7,8-Dimethoxy-4-phenyl-4H-1,3,4-triaza-phenalene

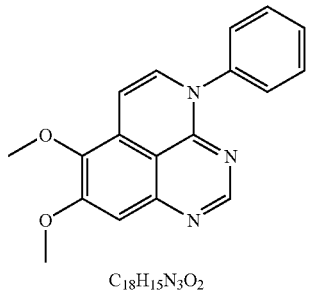

C$_{18}$H$_{15}$N$_3$O$_2$
MW 305.33

Step A: 7,8-Dimethoxy-4-phenyl-5,6-dihydro-4H-1,3,4-triaza-phenalen-5-ol

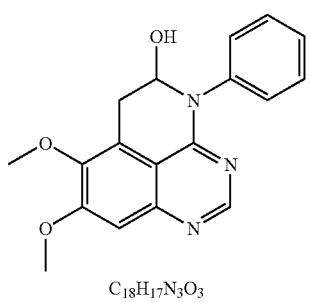

C$_{18}$H$_{17}$N$_3$O$_3$
MW 323.35

To a solution of (5-allyl-6,7-dimethoxy-quinazolin-4-yl)-phenyl-amine (0.35 g, 1.09 mmol) (from Example 15, Step E ,supra) in methanol (50 mL) at −78° C. was passed a continuous stream of O$_3$ until the color of the solution became blue. The reaction solution was then purged with argon, and methyl sulfide (5 mL) (Aldrich) was added. The reaction mixture was slowly warmed to room temperature and stirred overnight. The solution was concentrated, the residue was dried in vacuo to give the desired 7,8-dimethoxy-4-phenyl-5,6-dihydro-4H-1,3,4-triaza-phenalen-5-ol as a crude yellow solid. (Yield 0.17 g, 48%).

Step B: 7,8-Dimethoxy-4-phenyl-4H-1,3,4-triaza-phenalene

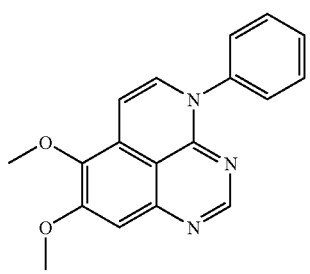

C$_{18}$H$_{15}$N$_3$O$_2$
MW 305.33

To a solution of 7,8-dimethoxy-4-phenyl-5,6-dihydro-4H-1,3,4-triaza-phenalen-5-ol (91 mg, 0.28 mmol) (from Example 20, Step A, supra) and triethylamine (0.23 mL, 1.69 mmol) in dichloromethane (50 mL) at 0° C. was added methanesulfonyl chloride (0.087 mL, 1.12 mmol) (Aldrich). The reaction solution was the stirred at room temperature for 2 hours. The solution was then concentrated, the residue was purified by chromatography using EtOAc/CH$_2$Cl$_2$/NEt$_3$ (1:4:0.05) as eluent to give the desired 7,8-dimethoxy-4-phenyl-4H-1,3,4-triaza-phenalene as a white solid. (Yield 47 mg, 55%).

Example 21

4-(4-Chloro-phenyl)-7,8-dimethoxy-4H-1,3,4-triaza-phenalene

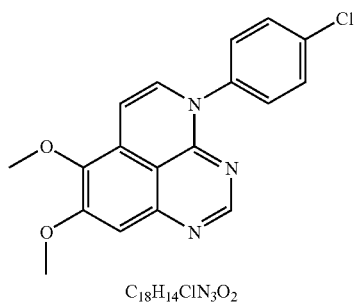

C$_{18}$H$_{14}$ClN$_3$O$_2$
MW 339.78

Step A: 7,8-Dimethoxy-4-phenyl-5,6-dihydro-4H-1,3,4-triaza-phenalen-5-ol

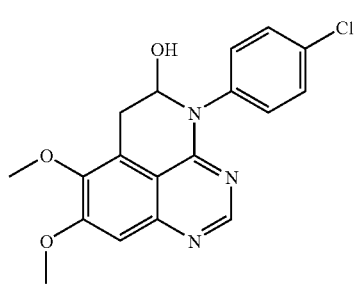

C$_{18}$H$_{16}$ClN$_3$O$_3$
MW 360

To a solution of (5-allyl-6,7-dimethoxy-quinazolin-4-yl)-(4-chloro-phenyl)-amine (0.14 g, 0.39 mmol) (from Example 16, Step E, supra), in methanol (50 mL) at −78° C. was passed a continuous stream of O$_3$ until the color of the solution became blue. The reaction solution was then purged with argon, and methyl sulfide (5 mL) (Aldrich) was added. The reaction mixture was slowly warmed to room temperature and stirred overnight. The solution was concentrated, the residue was dried in vacuo to give the desired 7,8-dimethoxy-4-(4-chloro-phenyl)-5,6-dihydro-4H-1,3,4-triaza-phenalen-5-ol as a crude yellow solid. (Yield 0.14 g, 100%).

Step B: 4-(4-Chloro-phenyl)-7,8-dimethoxy-4H-1,3,4-triaza-phenalene

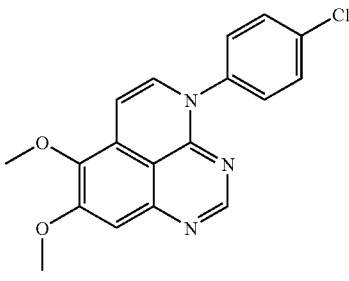

C$_{18}$H$_{14}$ClN$_3$O$_2$
MW 339.78

To a solution of 7,8-dimethoxy-4-(4-chloro-phenyl)-5,6-dihydro-4H-1,3,4-triaza-phenalen-5-ol (140 mg, 0.39 mmol) (from Example 21, Step A, supra) and triethylamine (0.32 mL, 2.33 mmol) in dichloromethane (50 mL) at 0° C. was added methanesulfonyl chloride (0.12 mL, 1.55 mmol) (Aldrich). The reaction solution was the stirred at room temperature for 2 hours. The solution was then concentrated, the residue was purified by chromatography using EtOAc/CH$_2$Cl$_2$/NEt$_3$ (1:1:0.01) as eluent to give the desired 4-(4-chloro-phenyl)-7,8-dimethoxy-4H-1,3,4-triaza-phenalene as a yellow solid. (Yield 47 mg, 55%).

Example 22

4-(3-Bromo-phenyl)-7,8-dimethoxy-4H-1,3,4-triaza-phenalene

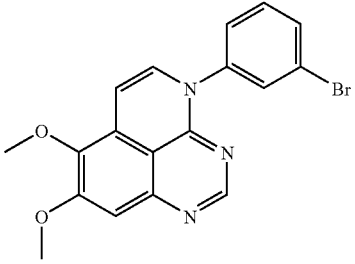

C$_{18}$H$_{14}$BrN$_3$O$_2$
MW 384.23

Step A: 7,8-Dimethoxy-4-(3-bromo-phenyl)-5,6-dihydro-4H-1,3,4-triaza-phenalen-5-ol

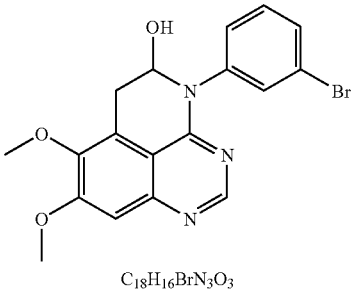

C$_{18}$H$_{16}$BrN$_3$O$_3$
MW 402.24

To a solution of (5-allyl-6,7-dimethoxy-quinazolin-4-yl)-(3-bromo-phenyl)-amine (0.17 g, 0.42 mmol) (from Example 17, Step E, supra) in methanol (50 mL) at −78° C. was passed a continuous stream of 03 until the color of the solution became blue. The reaction solution was then purged with argon, and methyl sulfide (5 mL) (Aldrich) was added. The reaction mixture was slowly warmed to room temperature and stirred overnight. The solution was concentrated, the residue was dried in vacuo to give the desired 7,8-dimethoxy-4-(3-bromo-phenyl)-5,6-dihydro-4H-1,3,4-triaza-phenalen-5-ol as a crude brown oil. (Yield 0.16g, 100%).

Step B: 4-(3-Bromo-phenyl)-7,8-dimethoxy-4H-1,3,4-triaza-phenalene

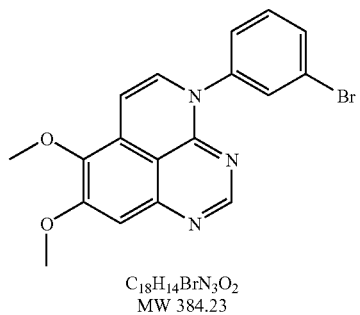

$C_{18}H_{14}BrN_3O_2$
MW 384.23

To a solution of 7,8-dimethoxy-4-(3-bromo-phenyl)-5,6-dihydro-4H-1,3,4-triaza-phenalen-5-ol (0.17 g, 0.42 mmol) (from Example 22, Step A, supra) and triethylamine (0.35 mL, 2.53 mmol) in dichloromethane (30 mL) at 0° C. was added methanesulfonyl chloride (0.13 mL, 1.68 mmol) (Aldrich). The reaction solution was stirred at room temperature for 2 hours. The solution was then concentrated, the residue was purified by chromatography using EtOAc/CH$_2$Cl$_2$/NEt$_3$ (1:1:0.01) as eluent to give the desired 4-(3-bromo-phenyl)-7,8-dimethoxy-4H-1,3,4-triaza-phenalene as an off white solid. (Yield 81 mg, 50%).

The pharmacological properties of the compounds of this invention may be confirmed by a number of pharmacological assays. The exemplified pharmacological assay that follows was carried out with the compounds according to the invention and their salts.

Example 23

Kinase Inhibition Assay

To determine the ability of test compounds according to the invention to inhibit EGFR activity, kinase assays were conducted using an HTRF (Homogeneous Time Resolved Fluorescence) assay. This assay is described in A. J. Kolb et. al., Drug Discovery Today, 1998, 3(7), p 333.

Kinase activity assays were performed in 96-well polypropylene plates (Falcon) with a total volume of 90 μL in each well. Each well contained 1 μM EGFR substrate (Biotin-EEEEYFELV), 1.5 nM EGFR, and a test compound with one of 8 assay concentrations ranging from 100 μM to 128 pM (1:5 serial dilution). The kinase activity assay was done in the presence of 100 mM HEPES, pH 7.4, 1 mM DTT, 5 mM MgCl$_2$, 2 mM MnCl$_2$, 1% DMSO, 0.5 μM ATP (K$_m$ for EGFR), 0.1 mM Na$_2$VO$_4$, and 0.02% BSA. The reaction was incubated at 37° C. for 30 minutes. To stop the EGFR reaction, 72 μL of reaction mixture was transferred into a STOP plate containing 18 μL of revelation buffer (20 mM EDTA, 50 mM HEPES, pH 7.4, 0.02% BSA, 10 nM Eu-labelled anti-pY antibody (final conc. 2 nM), and 100 nM streptavidin (final conc. 20 nM)). After mixing, 35 μL of solution was transferred into duplicate wells of a 384-well black plate (Costar), and read at 615/665 nm on a Wallac Victor 5 reader.

Test compound IC$_{50}$ values were determined from duplicate sets of data, and calculated by using Excel and fitting data to equation Y=[(a−b)/{1+(X/c)$^d$}+b, where a and b are enzyme activity in the presence of no test compound and an infinite amount of test compound, respectively, c is the IC$_{50}$ and d is the hill constant of the compound response. The IC$_{50}$ value is the concentration of test compound that reduces by 50% the enzyme activity under the test conditions described.

The compounds of the invention had IC$_{50}$ values of less than 1 μM when tested in the above-described assay. These compounds thus exhibited EGFR kinase inhibition activity.

What is claimed is:

1. A compound of the formula

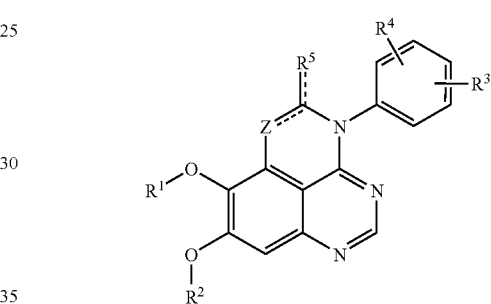

I wherein
Z is C or N;
R$^1$ and R$^2$ are independently selected from
H,
lower alkyl,
lower alkyl substituted with
OR$^6$,
NR$^6$R$^7$,
heterocycle, and
heteroaryl;
R$^3$ and R$^4$ are each independently selected from
H,
F,
Cl, and
Br;
R$^5$ is selected from
H,
OH,
SH,
oxo,
thione, and
C$_1$–C$_3$ alkyl; and
R$^6$ and R$^7$ are each independently selected from
H, and
lower alkyl
or, alternately NR$^6$R$^7$ together can form a ring having 3 to 7 atoms, said ring optionally including up to three additional heteroatoms and being optionally substituted by one or more lower alkyl;
or the pharmaceutically acceptable salts or esters thereof.

2. The compound of claim 1 wherein Z is C.

3. The compound of claim 1 wherein Z is N.

4. The compound of formula I, claim 1, wherein $R^1$ and $R^2$ are independently selected from lower alkyl.

5. The compound of claim 4 wherein either $R^1$ or $R^2$ is methyl.

6. The compound of claim 4 wherein both $R^1$ and $R^2$ are methyl.

7. The compound of formula I, claim 1, wherein $R^3$ and $R^4$ are independently selected from H, Br, Cl and F.

8. The compound of claim 7 wherein either $R^3$ or $R^4$ is H.

9. The compound of claim 7 wherein $R^3$ and $R^4$ are both H.

10. The compound of formula I, claim 1, wherein $R^6$ is selected from =O, =S, H and lower alkyl.

11. The compound of claim 10 wherein $R^5$ is selected from H and lower alkyl.

12. The compound of formula I, claim 1, wherein Z is N, $R^1$ and $R^2$ are methyl, and $R^3$ and $R^4$ are H.

13. The compound of formula I, claim 1, wherein Z is N, $R^1$ and $R^2$ are methyl, one of $R^3$ and $R^4$ is H and the other is Cl or Br.

14. The compound of formula I, claim 1, wherein Z is C, $R^1$ and $R^2$ are methyl, one of $R^3$ and $R^4$ is H and the other is Cl or Br.

15. The compound of formula I, claim 1, wherein Z is C, $R^1$ and $R^2$ are methyl, one of $R^3$ and $R^4$ is F and the other is Cl or Br.

16. A compound selected from the group
8,9-Dimethoxy-3-phenyl-1H,3H-1,3,4,6-tetraaza-phenalen-2-one;
8,9-Dimethoxy-3-phenyl-1H,3H-1,3,4,6-tetraaza-phenalene-2-thione;
8,9-Dimethoxy-3-phenyl-3H-1,3,4,6-tetraaza-phenalene;
8,9-Dimethoxy-2-methyl-3-phenyl-3H-1,3,4,6-tetraaza-phenalene; and
2-Ethyl-8,9-dimethoxy-3-phenyl-3H-1,3,4,6-tetraaza-phenalene.

17. A compound selected from the group
3-(3-Bromo-phenyl)-8,9-dimethoxy-3H-1,3,4,6-tetraaza-phenalene
3-(3-Bromo-phenyl)-8,9-dimethoxy-1H-3H-1,3,4,6-tetraaza-phenalen-2-one;
3-(3-Bromo-phenyl)-8,9-dimethoxy-2-methyl-3H- 1,3,4,6-tetraaza-phenalene;
3-(3-Bromo-phenyl)-8,9-dimethoxy-1H,3H-1,3,4,6-tetraaza-phenalen-2-thione;
3-(3-Bromo-phenyl)-2-ethyl-8,9-dimethoxy-3H-1,3,4,6-tetraaza-phenalene; and
3-(3-Chloro-phenyl)-8,9-dimethoxy-1H,3H-1,3,4,6-tetraaza-phenalen-2-one.

18. A compound selected from the group
3-(3-Chloro-phenyl)-8,9-dimethoxy-2-methyl-3H-1,3,4, 6-tetraaza-phenalene;
3-(4-Chloro-phenyl)-8,9-dimethoxy-3H-1,3,4,6-tetraaza-phenalene;
3-(4-Chloro-phenyl)-8,9-dimethoxy-1H,3H-1,3,4,6-tetraaza-phenalen-2-thione;
7,8-Dimethoxy-5-methyl-4-phenyl-4H-1,3,4-triaza-phenalene;
4-(4-Chloro-phenyl)-7,8-dimethoxy-5-methyl-4H-1,3,4-triaza-phenalene;
4-(3-Bromo-phenyl)-7,8-dimethoxy-5-methyl-4H-1,3,4-triaza-phenalene; and
4-(3-Bromo-phenyl)-7,8-dimethoxy-5-methyl-4H-1,3,4-triaza-phenalene.

19. A compound selected from the group
4-(4-Bromo-2-fluoro-phenyl)-7,8-dimethoxy-5-methyl-4H-1,3,4-triaza-phenalene;
7,8-Dimethoxy-4-phenyl-4H-1,3,4-triaza-phenalene;
4-(4-Chloro-phenyl)-7,8-dimethoxy-4H-1,3,4-triaza-phenalene; and
4-(3-Bromo-phenyl)-7,8-dimethoxy-4H-1,3,4-triaza-phenalene.

20. A pharmaceutical composition comprising as an active ingredient an effective amount of a compound of claim 1 and a pharmaceutically acceptable carrier or excipient.

21. The pharmaceutical composition of claim 20 which is suitable for parenteral administration.

22. A method for treating a solid tumor selected from a breast, colon, prostate or lung tumor comprising administering to a subject in need of such treatment a therapeutically effective amount of at least one compound according to claim 1.

* * * * *